United States Patent
Paris et al.

(10) Patent No.: US 7,605,149 B1
(45) Date of Patent: Oct. 20, 2009

(54) MODULATION OF THE PHOSPHOLIPASE A2 PATHWAY AS A THERAPEUTIC

(75) Inventors: Daniel Paris, Tampa, FL (US); Terrence C. Town, Lutz, FL (US); Michael J. Mullan, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/743,781

(22) PCT Filed: Jul. 13, 1999

(86) PCT No.: PCT/US99/15947

§ 371 (c)(1),
(2), (4) Date: Mar. 28, 2001

(87) PCT Pub. No.: WO00/02561

PCT Pub. Date: Jan. 20, 2000

Related U.S. Application Data

(60) Provisional application No. 60/092,570, filed on Jul. 13, 1998.

(51) Int. Cl.
*A61K 31/6615* (2006.01)
(52) U.S. Cl. ....................................................... 514/148
(58) Field of Classification Search ................ 514/256, 514/272, 277, 200, 148
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | LaZor | |
| 4,486,194 A | 12/1984 | Ferrara | |
| 4,487,603 A | 12/1984 | Harris | |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 4,925,678 A | 5/1990 | Ranney | |
| 4,959,217 A | 9/1990 | Sanders et al. | |
| 5,011,771 A | 4/1991 | Bellet et al. | |
| 5,167,616 A | 12/1992 | Haak et al. | |
| 5,169,383 A | 12/1992 | Gyory et al. | |
| 5,192,659 A | 3/1993 | Simons | |
| 5,225,182 A | 7/1993 | Sharma | |
| 5,272,057 A | 12/1993 | Smulson et al. | |
| 5,281,521 A | 1/1994 | Trojanowski et al. | |
| 5,700,816 A | 12/1997 | Isakson et al. | |
| 5,932,576 A | 8/1999 | Anantanarayan et al. | |
| 6,316,464 B1 * | 11/2001 | Cheng et al. | 514/300 |
| 6,436,983 B1 * | 8/2002 | Watanabe | 514/419 |

FOREIGN PATENT DOCUMENTS

| | | | |
|---|---|---|---|
| WO | 9503297 | * | 2/1995 |
| WO | 99/25340 | * | 5/1999 |

OTHER PUBLICATIONS

Jackson et al., The Journal of Pharmacology and Experimental Therapeutics, vol. 284, No. 2, 1998.*

Abramovitz, M., E. Wong, M.E. Cox, C.D. Richardson, C. Li, and P.J. Vickers. 5-lipoxygenase-activating protein stimulates the utilization of arachidonic acid by 5-lipoxygenase. *Eur. J. Biochem.* 215:105-11, 1993.

Arita, H., K. Hanasaki, T. Nakano, S. Oka, H. Teraoka, and K. Matsumoto. Novel proliferative effect of phospholipase A2 in Swiss 3T3 cells via specific binding site. *J. Biol. Chem.* 266:19139-41, 1991.

Basso, D., C. Fabris, M.P. Panozzo, T. Meggiato, G. Del Favero, and R. Naccarato. Serum phospholipase A2 activity in chronic pancreatic diseases. *Clin. Biochem.* 23:229-32, 1990.

(Continued)

*Primary Examiner*—Ardin Marschel
*Assistant Examiner*—James D Anderson

(57) ABSTRACT

There is provided a method of modifying vasoactivity by regulating a soluble Aβ pro-inflammatory pathway. Also provided is a method of modifying inflammatory reactions in microglia and neurons by regulating a soluble Aβ pro-inflammatory pathway. A method of treating patients with vascular disease by modifying an intracellular soluble Aβ pro-inflammatory pathway is also provided. A pharmaceutical composition consisting essentially of an effective amount of a soluble Aβ pro-inflammatory pathway regulator in a pharmaceutically effective carrier is also provided.

10 Claims, 11 Drawing Sheets

OTHER PUBLICATIONS

Borsch-Haubold, A.G., S. Pasquet, and S.P. Watson. Direct inhibition of cyclooxygenase-1 and -2 by the kinase inhibitors SB 203580 and PD 98059. SB 203580 also inhibits thromboxane synthase. *J. Biol. Chem.* 273:28766-72, 1998.

Clark, J.D., L.L. Lin, R.W. Kriz, C.S. Ramesha, L.A. Sultzman, A.Y. Lin, N. Milona, and J.L. Knopf.. A novel arachidonic acid-selective cytosolic PLA2 contains a Ca(2+)-dependent translocation domain with homology to PKC and GAP. *Cell* 65:1043-1051, 1991.

Crawford, F., Z. Suo, C. Fang, and M. Mullan. Characteristics of the in Vitro Vasoactivity of beta-amyloid peptides. *Exp. Neurol.* 150:159-168, 1998.

Dennis, E.A., S.G. Rhee, M.M. Billah, and Y.A. Hannun. Role of phospholipase in generating lipid second messengers in signal transduction. *FASEB J.* 5:2068-77, 1991.

Dennis, E.A. The growing phospholipase A2 superfamily of signal transduction enzymes. *Trends Biochem. Sci.* 22:1-2, 1997.

Duara, R., C. Grady, J. Haxby, M. Sundaram, N.R. Cutler, L. Heston, A. Moore, N. Schlageter, S. Larson, and S.I. Rapoport. Positron emission tomography in Alzheimer's disease. *Neurology* 36:879-887, 1986.

Dudley, D.T., L. Pang, S.J. Decker, A.J. Bridges, and A.R. Saltiel.. A synthetic inhibitor of the mitogen-activated protein kinase cascade. *Proc. Natl. Acad. Sci. U S A* 92:7686-9, 1995.

Ellis, R.J., J.M. Olichney, L.J. Thal, S.S. Mirra, J.C. Morris, D. Beekly, and A. Heyman. Cerebral amyloid angiopathy in the brains of patients with Alzheimer's disease: the CERAD experience, Paart XV. *Neurology* 46:1592-6, 1996.

Farooqui, A.A., S.I. Rapoport, and L.A. Horrocks. Membrane phospholipid alterations in Alzheimer's disease: deficiency of ethanolamine plasmalogens. *Neurochem. Res.* 22:523-7, 1997.

Futaki, N., S. Takahashi, M. Yokoyama, I. Arai, S. Higuchi, and S. Otomo. NS-398, a new anti-inflammatory agent, selectively inhibits prostaglandin G/H synthase/cyclooxygenase (COX-2) activity in vitro. *Prostaglandins* 47:55-9, 1994.

Glover, S., M.S. de Carvalho, T. Bayburt, M. Jonas, E. Chi, C.C. Leslie, and M.H. Gelb. Translocation of the 85-kDa phospholipase A2 from cytosol to the nuclear envelope in rat basophilic leukemia cells stimulated with calcium ionophore or IgE/antigen. *J. Biol. Chem.* 270:15359-67, 1995.

Gravitt, K.R., N.E. Ward, and C.A. O'Brian.. Inhibition of protein kinase C by melittin: antagonism of binding interactions between melittin and the catalytic domain by active-site binding of MgATP. *Biochem. Pharmacol.* 47:425-7, 1994.

Griffin, W.S.T., J.G. Sheng, G.W. Roberts, and R.E. Mrak. Interleukin-1 expression in different plaque types in Alzheimer's disease: significance in plaque evolution. *J. Neuropathol. Exp. Neurol.* 54:276-281, 1995.

Han, S.K., B.I. Lee, and W. Cho. Bacterial expression and characterization of human pancreatic phospholipase A2. *Biochim. Biophys. Acta.* 1346:185-92, 1997.

Hanasaki, K., Y. Yokota, J. Ishizaki, T. Itoh, and H. Arita. Resistance to endotoxic shock in phospholipase A2 receptor-deficient mice. *J. Biol. Chem.* 272:32792-7, 1997.

Hernandez, M., S.L. Burillo, M.S. Crespo, and M.L. Nieto. Secretory phospholipase A2 activates the cascade of mitogen-activated protein kinases and cytosolic phospholipase A2 in the human astrocytoma cell line 1321N1. *J. Biol. Chem.* 273:606-12, 1998.

Husain, S., and A.A. Abdel-Latif. Role of protein kinase C alpha in endothelin-1 stimulation of cytosolic phospholipase A2 and arachidonic acid release in cultured cat iris sphincter smooth muscle cells. *Biochim. Biophys. Acta.* 1392-127-44, 1998.

Huwiler, A., G. Staudt, R.M. Kramer, and J. Pfeilschifter. Cross-talk between secretory phospholipase A2 and cytosolic phospholipase A2 in rat renal mesangial cells. *Biochim. Biophys. Acta.* 1348:257-72, 1997.

Iadecola, C., F. Zhang, K. Niwa, C. Eckman, S.K. Turner, E. Fischer, S. Younkin, D.R. Borchelt, K.K. Hsiao, and G.A. Carlson. SOD1 rescues cerebral endothelial dysfunction in mice overexpressing amyloid precursor protein. *Nat. Neurosci.* 2:157-61, 1999.

Ishizaki, J., K. Hanasaki, K. Higashino, J. Kishino, N. Kikuchi, O. Ohara, and H. J. Arita. Molecular cloning of pancreatic group I phospholipase A2 receptor. *Biol. Chem.* 269:5897-904, 1994.

Itagaki, S., P.L. McGeer, H. Akiyama, S. Zhu, and D. Selkoe. Relationship of microglia and astrocytes to amyloid deposits of Alzheimer disease. *J. Neuroimmunol.* 24:173-182, 1989.

Iversen, L.L., R.J. Mortishire-Smith, S.J. Pollack, and M.S. Shearman, The toxicity in vitro of beta-amyloid protein. *Biochem. J.* 311:1-16, 1995.

Iwamoto, N., K. Kobayashi, and K. Kosaka. The formation of prostaglandins in the postmortem cerebral cortex of Alzheimer-type dementia patients. *J. Neurol.* 236:80-4, 1989.

Jeandel, C., M.B. Nicolas, F. Dubois, F. Nabet-Belleville, F. Penin, and G. Cuny. Lipid peroxidation and free radical scavengers in Alzheimer's disease. *Gerontology* 35:275-82, 1989.

Johnson, K.A., S.T. Mueller, T.M. Walshe, R.j. English, and B.L. Holman. Cerebral perfusion imaging in Alzheimer's disease. Use of a single photon emission computed tomography and iofetamine hydrochloride I 123. *Arch. Neurol.* 44:165-168, 1987.

Joyce-Brady, M., J.B. Rubins, M.P. Panchenko, J. Bernardo, M.P. Steele, L. Kolm, E.R Simons, and B.F. Dickey. Mechanisms of mastoparan-stimulated surfactant secretion from isolated pulmonary alveolar type 2 cells. *J. Biol. Chem.* 266:6859-65, 1991.

Kan, H., Y. Ruan, and K.U. Malik. Involvement of mitogen-activated protein kinase and translocation of cytosolic phospholipase A2 to the nuclear envelope in acetylcholine-induced prostacyclin synthesis in rabbit coronary endothelial cells. *Mol. Pharmacol.* 50:1139-47, 1996.

Kanemasa, T., K. Hanasaki, and H. Arita.. Migration of vascular smooth muscle cells by phospholipase A2 via specific binding sites. *Biochim. Biophys. Acta.* 1125:210-4, 1992.

Kishino, J., O. Ohara, K. Nomura, R.M. Kramer, and H. Arita. Pancreatic-type phospholipase A2 induces group II phospholipase A2 expression and prostaglandin biosynthesis in rat mesangial cells. *J. Biol. Chem.* 269:5092-8, 1994.

Klinker, J.F., K.L. Laugwitz, A. Hageluken, and R. Seifert. Activation of GTP formation and high-affinity GTP hydrolysis by mastoparan in various cell membranes. G-protein activation via nucleoside diphosphate kinase, a possible general mechanism of mastoparan action. *Biochem. Pharmacol.* 51:217-23, 1996.

Kundu, G.C., and A.B. Mukherjee. Evidence that porcine pancreatic phospholipase A2 via its high affinity receptor stimulates extracellular matrix invasion by normal and cancer cells. *J. Biol. Chem.* 272:2346-53, 1997.

Kuo, Y., M. Emmerling, C. Vigo-Pelfrey, T.C. Kasunic, J.B. Kirkpatrick, G.H. Murdoch, M.J. Ball, and A. Roher. Water-soluble Abeta (N-40, N-42) Oligomers in Normal and Alzheimer Disease Brains. *J. Biol. Chem.* 271:4077-4081, 1996.

Kuo, Y., M. Emmerling, H. Lampert, S.R. Hempelman, T.A. Kokjohn, A.S. Woods, R.J. Cotter, and A. Roher. High Levels of Circulating Abeta42 are Sequestered by Plasma Proteins in Alzheimer's Disease. *Biochem. Biophys. Res. Comm.* 257:787-791, 1999.

Lambeau, G., P. Ancian, J. Barhanin, and M. J. Lazdunski. Cloning and expression of a membrane receptor for secretory phospholipases A2. *Biol. Chem.* 269:1575-8, 1994.

Lehtonen, J.Y., J.M. Holopainen, and P.K. Kinnunen. Activation of phospholipase A2 by amyloid beta-peptides in vitro. *Biochemistry* 35:9407-14, 1996.

Lim, A., Tsuang, D., Kukull, W., Nochlin, D., Leverenz, James, McCormick, W., Bowen, J., Teri, L., Thompson, J., Peskind, E., Raskind, M., Larson, E. Clinico-Neuropathological Correlation of Alzheimer's Disease in a Commmunity-Cased Case Series, JAGS 47:564-599, 1999.

Lin, L.L., M. Wartmann, A.Y. Lin, J.L. Knopf, A. Seth, and R.J. Davis. cPLA2 is phosphorylated and activated by MAP kinase. *Cell* 72:269-78, 1993.

Lue, L.F., L. Brachova, W.H. Civin, and J. Rogers. Inflammation, Abeta deposition, and neurofibrillary tangle formation as correlates of Alzeimer's disease neurodegeneration. *J. Neuropathol. Exp. Neurol.* 55:1083-1088, 1996.

McGeer, P.L., M. Schulzer, and E.G. McGeer. Arthritis and anti-inflammatory agents as possible protective factors for Alzheimer's disease: a review of 17 epidemiologic studies. *Neurology* 47:425-432, 1996.

McGeer, P.L., and E.G. McGeer. Inflammation of the brain in Alzheimer's disease: implication for therapy. *J. Leukoc. Biol.* 65:409-15, 1999.

Minami, T., H. Tojo, Y. Shinomura, T. Komatsubara, Y. Matsuzawa, and M. Okamoto Elevation of phospholipase A2 protein in sera of patients with Crohn's disease and ulcerative colitis. *Am. J. Gastroenterol.* 88:1076-80, 1993.

Mirra, S.S., Gearing, M., McKeel, D.W. Jr., Crain, B.J. Hughes, J.P. van Belle, G., Heyman, A., and participating Neuopathologists. Interlaboratory Comparison of Neuropathology Assessments in Alzheimer's Disease: A Study of the Consortium to Establish a Registry for Alzheimer's Disease (CERAD), vol. 53, No. 3, pp. 303-315, May 1994.

Morita, I., M. Schindler, M.K. Regier, J.C. Otto, T. Hori, D.L. DeWitt, and W.L. Smith. Different intracellular locations for prostaglandin endoperoxide H synthase-1 and -2. *J. Biol. Chem.* 270:10902-8, 1995.

Murakami, M., S. Shimbara, T. Kambe, H. Kuwata, M.V. Winstead, J.A. Tischfield, and I. Kudo. The functions of five distinct mammalian phospholipase A2S in regulating arachidonic acid release. Type IIa and type V secretory phospholipase A2S are functionally redundant and act in concert with cytosolic phospholipase A2. *J. Biol. Chem.* 273:14411-23, 1998.

Naidu, A., D. Quon, and B. Cordell. beta-Amyloid peptide produced in vitro is degraded by proteinases released by cultured cells. *J. Biol. Chem.* 270:1369-74, 1995.

Nakajima, M., K. Hanasaki, M. Ueda, and H. Arita. Effect of pancreatic type phospholipase A2 on isolatd porcine cerebral arteries via its specific binding sites. *FEBS Lett* 309:261-4, 1992.

Nitsch, R.M., J.K. Blusztajn, A.G. Pittas, B.E. Slack, J.H. Growdon, and R.J. Wurtman. Evidence for a membrane defect in Alzheimer disease brain. *Proc. Natl. Acad. Sci. U S A* 89:1671-5, 1992.

Nomura, K., H. Fujita, and H. Arita. Gene expression of pancreatic-type phospholipase-A2 in rat ovaries: stimulatory action on progesterone release. *Endocrinology* 135:603-9, 1994.

Okamoto, T., S. Takeda, Y. Murayama, E. Ogata, and I. Nishimoto. Ligand-dependent G protein coupling function of amyloid transmembrane precursor. *J. Biol. Chem.* 270:4205-8, 1995.

Paris, D., T.A. Parker, T. Town, Z. Suo, C. Fang, J. Humphrey, F. Crawford, and M. Mullan. Role of Peroxynitrite in the Vasoactive and Cytotoxic Effects of Alzheimer's beta-amyloid1-40 Peptide. *Exp. Neurol.* 152:116-122, 1998.

Paris, D., T. Town, T.A. Parker, J. Humphrey, and M. Mullan. Isoform-specific vasoconstriction induced b Apolipoprotein E and modulation of this effect by Alzheimer's beta-amyloid peptide. *Neurosci. Lett.* 256:73-76, 1998.

Paris, D., T. Town, T.A. Parker, J. Tan, J. Humphrey, F. Crawford, and M. Mullan. Inhibition of Alzheimer's beta-Amyloid Induced Vasoactivity and Proinflammatory Response in Microglia by a cGMP-Dependent Mechanism. *Exp. Neurol.* 157:211-221, 1999.

Rogers, J., L.C. Kirby, S.R. Hempielman, et al. Clinical trial of indomethacin in Alzheimer's disease. *Neurology* 43:1609-1611, 1993.

Selkoe, D.J. Amyloid beta-protein and the genetics of Alzheimer's disease. *J. Biol. Chem.* 271:18295-8, 1996.

Serhan, C.N., J.Z. Haeggstrom, and C.C. Leslie. Lipid mediator networks in cell signaling: update and impact of cytokines. *FASEB J.* 10:1147-58, 1996.

Sisodia S.S., and D.L. Price. Role of the beta-amyloid protein in Alzheimer's disease. *FASEB J.* 9:366-70, 1995.

Stephenson, D.T., C.A. Lemere, D.J. Selkoe, and J.A. Clemens. Cytosolic phospholipase A2 (cPLA2) immunoreactivity is elevated in Alzheimer' disease brain. *Neurobiol. Dis.* 3:51-63, 1996.

Stewart, W.F., C. Kawas, M. Corrada, and E.J. Metter, Risk of Alzheimer's disease and duration of NSAID use. *Neurology* 48:626-632, 1997.

Suo, Z., J. Humphrey, A. Kundtz, F. Sethi, A. Placzek, F. Crawford, and M. Mullan. Soluble Alzheimer's beta-amyloid constricts the cerebral vasculature in vivo, *Neurosci. Lett.* 257:77-80, 1998.

Thomas, T., G. Thomas, C. McLendon, T. Sutton, and M. Mullan. beta-Amyloid-mediated vasoactivity and vascular endothelial damage. *Nature* 380:168-71, 1996.

Tischfield, J.A. A reassessment of the low molecular weight phospholipase A2 gene family in mammals. *J. Biol. Chem.* 272:17247-50, 1997.

Tohkin, M., J. Kishino, J. Ishizaki, and H. Arita. Pancreatic-type phospholipase A2 stimulates prostaglandin synthesis in mouse osteoblastic cells (MC3T3-E1) via a specific binding site. *J. Biol. Chem.* 268:2865-71, 1993.

Tsunoda, Y., and C. Owyang. The regulatory site of functional GTP binding protein coupled to the high affinity cholecystokinin receptor and phospholipase A2 pathway is on the G beta subunit of Gq protein in pancreatic acini. *Biochem. Biophys. Res. Commun.* 211:648-55, 1995.

Walker, D.G., O. Yasuhara, P.A. Patston, E.G. McGeer, and P.L. McGeer. Complement C1 inhibitor is produced by brain tissue and is cleaved in Alzheimer disease. *Brain. Res.* 675:75-82, 1995.

Wisniewski, H.M., and J. Weigel. Migration of perivascular cells into the neuropil and their involvement in beta-amyloid plaque formation. *Acta. Neuropathol. (Berl.)* 85:586-95, 1993.

Wisniewski, H.M., J. Wegiel, K.C. Wang, and B. Lach. Ultrastructural studies of the cells forming amyloid in the cortical vessel wall in Alzheimer's disease. *Acta. Neuropathol. (Berl.)* 84:117-27, 1992.

Zhu, M., C.H. Gelband, J.M. Moore, P. Posner, and C. Sumners. Angiotensin Type 2 Receptor Stimulation of Neuronal Delayed-Rectifier Potassium Current Involves Phospholipase A2 and Arachidonic Acid. *J. Neurosci.* 18:679-686, 1998.

Coria, F., A. Moreno, I. Rubio, M.A. Garcia, E. Morato, and F. Mayor. The cellular pathology associated with Alzheimer B-amyloid deposits in non-demented aged individuals. *Neuropathol. Appl. Neurobiol.* 19:261-268, 1993.

Lindahl, M., and C. Tagesson. Selective inhibition of group II phospholipase A2 by quercetin. *Inflammation* 17:573-82, 1993.

Crawford et al., Characteristics of the in Vitro Vasoactivity of B-amyloid Peptides, Experimental Neurology 150, 159-168 (1998), Article No. EN976743.

* cited by examiner

MODULATION OF THE PHOSPHOLIPASE A2 PATHWAY AS A THERAPEUTIC

CROSS REFERENCE TO RELATED APPLICATIONS

This patent application is a National Phase concerning a filing under 35 U.S.C. 371, claiming the benefit of priority of U.S. Provisional Application Ser. No. 60/092,570, filed Jul. 13, 1998, which is incorporated herein by reference.

BACKGROUND OF THE INVENTION

1. Field of the Invention

The present invention relates to methods and compositions to reduce the neuronal cell death associated with the pro-inflammatory pathway and vasoactivity. More specifically, the present invention relates to specific modulation of signal transduction pathways, such as the sPLA$_2$/MAPK/cPLA$_2$/AA/LOX/COX pathway, to reduce the pro-inflammatory response that leads to an enhanced production of eicosanoids.

2. Description of Related Art

The protein β-amyloid (A4, Aβ, Aβ$_{1-39-42}$) has long been central to the neuropathology of Alzheimer's disease (Glenner and Wong, 1984). However, its role in the disease process of Alzheimer's disease and other diseases, as well as its mechanism of action, remains in dispute.

It is undisputed that β-amyloid protein is a major component of the neuritic plaques which, along with the neurofibrillary tangles, provide the neuropathological diagnostic markers for Alzheimer's disease (Mattson, 1995; Vantner et al., 1991). It is also deposited around cerebral blood vessels in Alzheimer's disease (Scholz, 1938; Mandybur, 1975; Vinters, 1987).

The sequence for -amyloid is known (Glenner et al. 1984).

Emphasis has been on Alzheimer's being a neurological disease, not a vascular disease.

It has been suggested in Alzheimer's disease pathogenesis that β-amyloid has putative neurotoxic properties. However, there has been no consistent detection of such neurotoxic effects and there are conflicting reports (Price et al. 1992).

Referring to Teller et al. (1996), deposits of insoluble fibrils of amyloid -peptide (A) in the brain is a prominent neuropathological feature of all forms of Alzheimer's Disease (AD) regardless of the genetic predisposition of the subject. In addition to the deposition of A in senile plaques and neurofibrillary tangles, vascular amyloid deposition resulting in cerebral amyloid angiopathy is a hallmark of AD and related disorders such as Down's Syndrome. The abnormal accumulation of A is due to either over expression or altered processing of amyloid precursor protein (APP), a transmembrane glycoprotein. Soluble A containing forty amino acids (A$_{40}$) and to a lesser degree the peptide with forty-two amino acids (A$_{42}$) forms the core of the amyloid deposits. The APP gene is highly conserved across different species and APPmRNA has been detected in all tissues, suggesting a normal physiologic role for A. The cellular origin of A deposited in the brain or cerebral blood vessels in AD or its precise role in the neurodegenerative process has not been established.

Epidemiologic studies have demonstrated that anti-inflammatory therapy may be useful in the treatment of AD since a lower than expected prevalence or delayed onset of AD is apparent in patient populations using non-steroidal anti-inflammatory drugs (McGeer and McGeer, 1999; Rogers et al., 1993; and Stewart et al., 1997). Although the initiating event leading to AD-associated neuroinflammation remains speculative, the occurrence of immune system proteins, activated microglia and astrocytes among perivascular senile plaques suggests a possible involvement of Aβ in the induction of this inflammatory process (Coria et al., 1993; Griffin et al., 1995; Itagaki et al., 1989; Lue et al., 1996).

Arachidonic acid (AA) release and production of eicosanoids are prerequisites for inflammation, and phospholipase A$_2$s (PLA$_2$s) are key enzymes that initiate the AA cascade, which leads to the generation of multiple eicosanoid products during both acute and chronic inflammation. PLA$_2$ activity has been shown to be elevated in disease states with a strong inflammatory component, such as rheumatoid arthritis and septic shock (Basso et al., 1990; Morita et al., 1995). PLA$_2$s can be subdivided into several groups based upon their structures and enzymatic characteristics (Dennis, 1997). Secretory PLA$_2$s (sPLA2s) are low molecular mass (~14 kDa) enzymes that require a millimolar concentration of Ca$^{2+}$ to exert their enzymatic action and have little fatty acid selectivity when assayed in vitro (Tischfield, J. A., 1997). Cytosolic PLA$_2$ (cPLA$_2$) is an ubiquitously distributed 85-kDa enzyme, and requires a submicromolar concentration of Ca$^{2+}$ for effective hydrolysis of its substrate, AA-containing glycerophospholipids (Clark et al., 1991). The N-terminal CALB domain is responsible for Ca$^{2+}$-dependent translocation of cPLA$_2$ from the cytosol to perinuclear and endoplasmic reticular membranes (Glover et al., 1995), where several eicosanoid-generating enzymes, such as the two cyclooxygenases (COX-1 and COX-2) and 5-lipoxygenase (5-LOX), are located (Morita et al., 1995). Cytosolic PLA$_2$ has multiple phosphorylation sites, among which the mitogen-activated protein kinase-directed site (Ser$^{505}$) is the most critical for its activation (Lin et al, 1993).

Abnormal phospholipid metabolism has been found in AD brains, where changes were reported in concentrations of membrane phospholipids, their precursors, and catabolites, which could be evidence for abnormal PLA$_2$ activity in these patients (Farooqui et al., 1997; Nitsch et al., 1992). Moreover, marked increases have been reported in the levels of prostaglandins and lipid peroxides in AD brain (Iwamoto et al., 1989; Jeandel et al., 1989), both products of PLA$_2$ activity. Elevated cPLA$_2$ immunoreactivity (Stephenson et al., 1996) has been reported in association with amyloid deposits in the cortex of AD brain, supporting the hypothesis that there is an active inflammatory process occurring in AD. Furthermore, soluble Aβ$_{1-42}$ (in the pM to nM range) in a cell-free system has been shown to activate sPLA$_2$ (Lehtonen et al., 1996), suggesting that Aβ may exert its effects either on the substrate or directly on sPLA$_2$.

Using intact rat aortae in a tissue bath system, it was previously reported that Aβ peptides are vasoactive, and suggested that this vasoactivity could contribute to Alzheimer's pathology by reducing cerebral blood flow (Thomas et al., 1996). It has also been shown that Aβ peptides are able to enhance the vasoconstriction induced by endothelin-1 (ET-1), a potent endogenous vasoconstrictor responsible for control of cerebral vasotonus (Crawford et al., 1998) via a mechanism independent of reactive oxygen species (Paris et al., 1998). Furthermore, it was demonstrated that intra-arterial infusion of Aβ results in reduced cerebral blood flow in vivo (Suo et al., 1998), and similar impaired cerebral blood flow has been shown in transgenic mice which endogenously overproduce Aβ peptides (Iadecola, et al., 1999).

It would therefore be useful to detail the molecular mechanisms responsible for Aβ's enhancement of ET-1-induced vasoconstriction. It would also be useful to develop a method and pharmaceutical composition for counteracting such a pathway.

SUMMARY OF THE INVENTION

According to the present invention, there is provided a method of modifying vasoactivity by regulating a soluble Aβ pro-inflammatory pathway. Also provided is a method of treating patients with vascular disease by modifying an intracellular soluble Aβ pro-inflammatory pathway. Also provided is a method of modifying inflammatory reactions in microglia and neurons by regulating a soluble Aβ pro-inflammatory pathway. A pharmaceutical composition consisting essentially of an effective amount of an Aβ pro-inflammatory pathway regulator in a pharmaceutically effective carrier is also provided.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
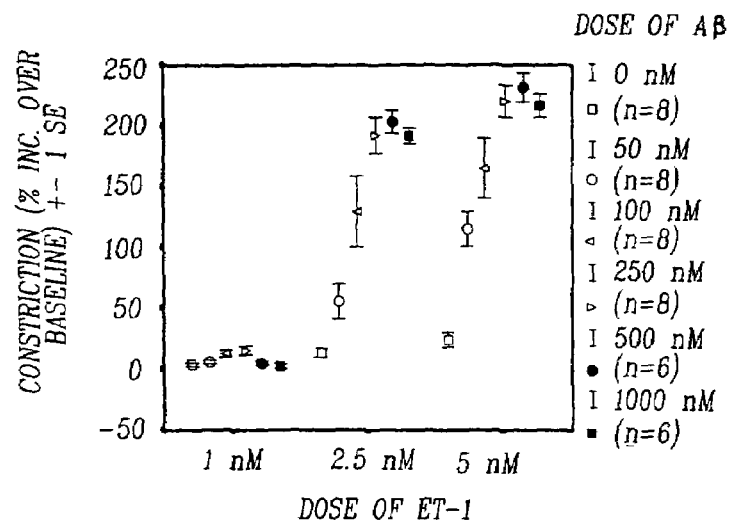
FIG. 1 is a graph showing the dose response curve showing $A\beta_{1-40}$ vasoactivity.

Generally, the present invention relates to a method and pharmaceutical composition for modifying the soluble Aβ pro-inflammatory pathway. Also provided is a method for treating patients with vascular disease (i.e. cerebral amyloid angiopathy, vascular amyloidosis, etc.) by modifying the intracellular Aβ pro-inflammatory pathway. More specifically, the present invention provides a method and composition for modifying the Aβ vasoactivity by antagonizing the $sPLA_2$/MAPK/$cPLA_2$/AA/LOX/COX pathway. Also provided is a method of modifying inflammatory reactions in microglia and neurons by regulating a soluble Aβ pro-inflammatory pathway.

It is generally thought that the Alzheimer Aβ peptides play an essential role in the pathogenesis of this disease, although the detailed mechanisms of neurodegeneration are not known. For instance, although deposits of Aβ are required for neuropathological diagnosis of AD by definition, this does not necessarily infer that the deposited form is pathologic. It is quite possible that soluble forms of Aβ are pathogenic. Soluble Aβ peptides display vasoactive properties, for instance by significantly enhancing the vasoconstriction elicited by an endogeneous cerebral vasoconstriction, endothelin-1 (ET-1). This phenomenon is exploited in the present invention and utilized a vessel bath system in order to delineate the specific signal transduction pathway leading to Aβ vasoactivity as shown in the Example herein.

The data demonstrate that Aβ(1-40) and Aβ(1-42) mediate vasoactivity by an activation of PLA2 through a stimulation of G-protein. The arachidonic acid product of PLA2 is metabolized essentially through two distinct pathways: cyclooxygenases and lipoxygenases. It is shown herein that the vasoactive properties of Aβ(1-40) and Aβ(1-42) are mediated by 5-lipoxygenase and by cyclo-oxygenase-2.

As an extension of these findings in a non-vascular system, there is shown that addition of Aβ(1-40) to microglial cells stimulates leukotriene B4 release (a major metabolite of 5-lipoxygenase) and AA release. Additionally, soluble Aβ peptides promote AA release from cultured neurons (NGF-β differentiated PC12 cells). Furthermore, drugs which oppose the pathway activated by soluble Aβ peptides oppose soluble Aβ-induced microglial LTB4 release. Taken together, these data show that soluble Aβ(1-40) and Aβ (1-42) induce a pro-inflammatory response pathway that leads to an enhanced production of AA and eicosanoids.

These findings demonstrate that the effect of Aβ can be modulated by manipulating specific signal transduction pathways providing the basis for novel therapeutic interventions. Specifically, drugs which modulate the phospholipase A2/arachidonic acid/5-lipoxygenase/cyclo-oxygenase-2 (PLA2/AA/5-LOX/COX-2) pro-inflammatory pathway are used in the practice of the present invention. Any drug that specifically opposes activation of the PLA2/AA/5-LOX/

COX-2 pathway reducing Aβ-induced vasoconstriction and hypoperfusion can be utilized in the practice of the invention.

The pharmaceutical compositions or drugs include, but are not limited to, antagonists of PLA2 stimulation such as those that oppose G-protein activation of PLA2. They can include compositions which directly inhibit PLA2 or drugs which inhibit 5-LOX or COX-2. Isotetrandrine is a specific G-protein inhibitor which can be used.

The present invention further provides for the administration of antagonists/drugs of the PLA2/AA/5-LOX/COX-2 pro-inflammatory pathway in the treatment of hypertension which is genetically linked to PLA2 (Frossard, PM, and Lestringant, GG (1995)), and genetically linked to $G_i$-protein (Siffert et al.) Further, the present invention provides for the administration of antagonists/drugs of the PLA2/AA/5-LOX/COX-2 pathway/cascade in the treatment of vasospasm associated with severe post-traumatic head injury.

The present invention therefore provides therapeutics which modulate (such as antagonists) signal transduction pathways, such as PLA2/AA/5-LOX/COX-2, to reduce the pro-inflammatory response that leads to an enhanced production of leukotrienes. The term antagonist or antagonizing is used in its broadest sense. Antagonism can include any mechanism or treatment which results in inhibition, inactivation, blocking or reduction of the signal pathway. For example, the antagonizing step can include blocking PLA-2 activation.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 µg/kg to 10 mg/kg per day.

The above discussion provides a factual basis for the use of methods and pharmaceutical compositions for modifying vasoactivity by regulating the soluble Aβ pro-inflammatory pathway. The methods used with and the utility of the present invention can be shown by the following non-limiting examples and the accompanying figures.

EXAMPLES

General Methods:

General methods in molecular biology: Standard molecular biology techniques known in the art and not specifically described are generally followed as in Sambrook et al., *Molecular Cloning: A Laboratory Manual,* Cold Springs Harbor Laboratory, New York (1989, 1992), and in Ausubel et al., *Current Protocols in Molecular Biology,* John Wiley and Sons, Baltimore, Md. (1989). Polymerase chain reaction (PCR) is carried out generally as in *PCR Protocols: A Guide To Methods And Applications,* Academic Press, San Diego, Calif. (1990). Reactions and manipulations involving other nucleic acid techniques, unless stated otherwise, are performed as generally described in Sambrook et al., 1989, *Molecular Cloning: A Laboratory Manual,* Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Immunoassays

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual,* Cold Springs Harbor, N.Y., 1989.

Example 1

The following example demonstrates that soluble Alzheimer's β-amyloid peptides mediate vasoactivity through a pro-inflammatory pathway, the phospholipase A2/arachidonic acid/5-lipoxygenase/cyclo-oxygenase-2 cascade. Furthermore, this example shows that blocking specific target molecules on this pathway oppose the effect of soluble Aβ peptides (1-40 and 1-42) in the vasculature.

Materials and Methods

The compounds used in vasoactivity assays include: Porcine pancreatic $PLA_2$ ($sPLA_2$), melittin, mastoparan and ET-1 were purchased from Sigma. Isotetrandrine, MK-886, RHC-80267, diacylglycerol (DAG), oleyloxyethylphosphocholine (oleylox.), bisindolylmaleimide I (bisindol.), PD98059, SB202190, methyl arachidonyl fluophosphonate (MAFP), quercetin, haloenol lactone suicide substrate (HELSS), AACOCF3 and NS-398 were obtained from Calbiochem. $Aβ_{1-40}$ and $Aβ_{1-42}$ were obtained from QCB. MK-886, RHC-80267, DAG, bisindol., PD98059, SB202190, MAFP, quercetin, HELSS, AACOCF3, NS-398, $Aβ_{1-40}$ and $Aβ_{1-42}$ and oleylox. were dissolved in DMSO, whereas melittin, mastoparan and ET-1 were dissolved in HPLC grade water, and $sPLA_2$ was dissolved in Kreb's buffer.

Vessel experiments. Freshly dissected aortae were prepared from normal male Sprague-Dawley rats (7-8 months old, purchased from Zivic Miller, Zelienople, Pa.) as previously described by Paris et al, Exp Neurol 1998 and Exp Neurol 1999. Rat aortae were segmented into rings and suspended in Kreb's buffer on hooks connected to a tensiometer linked to a MacLab system. Aortic rings were equilibrated for 2 hours, in 7 mL tissue baths containing Kreb's buffer oxygenated with 95% $O_2$: 5% $CO_2$, and thermoregulated to 37° C. A baseline tension of 2 g was applied to each ring, and the first set of aortic rings was pretreated with the various compounds named above either alone or in combination with Aβ peptides. After 5 minutes of incubation in the presence or absence of Aβ, this first set of vessels was subjected to a dose range of ET-1 (from 1 nM to 5 nM). A second set of vessels was treated with 1 μM of Aβ peptides prior to the addition of ET-1. A third set (control) received only ET-1 treatment. Each ET-1 dose was added only after the constriction response to the previous dose had reached a plateau. In all cases the means ±1 standard error (SE) of the percentage vasoconstriction increase over baseline were determined for each dose of ET-1 used.

Measurement of [$^3$H]AA release in intact rat aortae. Aortic rings (1.5 mm long) were placed in 1 mL of physiological saline solution (PSS, containing 130 mM NaCl, 5 mM KCl, 1.5 mM $CaCl_2$, 1.2 mM $MgCl_2$, 10 mM HEPES, and 10 mM glucose adjusted to pH 7.2 with NaOH) and incubated with 2.5 μCi of [$^3$H]AA (specific activity of 91.8 Ci/mmol) for 24 h at 4° C. Rat aortae were subsequently washed in 50 mL of Kreb's buffer and then subjected to the vasoactivity assay. Initial background [$^3$H]AA release was determined following 30 min of equillibration for each aortic ring prior to treatment by removing 200 μL of Kreb's buffer (total volume of 7 mL each) from each bath, and measuring radioactivity (in cpm) after the addition of 1 mL of scintillant (EcoLume, ICN Inc., Calif.) using a liquid scintillation counter (1209 Rackbeta, WALLAC Inc., Md.). Subsequently, aortic rings were treated with $sPLA_2$ alone or $Aβ_{1-40}$ (1 μM) in the presence or absence of a MEK1/2 inhibitor (PD 98059) or a $cPLA_2$ inhibitor (AACOCF3) for 5 min, or went untreated for the same length of time (control). Quantification of [$^3$H]AA release was then preformed as described above. All aortic rings were then subjected to a dose range of ET-1 (1, 2.5, and 5 nM), and radioactivity was measured 5 min after the first dose of ET-1 (1 nM), and 20 min after the second (2.5 nM) and third (5 nM) doses of ET-1. Radioactivity incorporated into each ring was determined by placing the aortic ring in 1 mL of scintillant and assaying as described above. Results are expressed as the means ±1 SE of the percentage of [$^3$H]AA incorporated for each aortic ring [([$^3$H]AA released—[$^3$H]AA initial background)/incorporated [$^3$H]AA].

Statistical analysis. Analysis of variance (ANOVA) was used to analyze the data, with post-hoc comparisons of means carried out where appropriate by Sheffe's or Bonferonni's methods. As previously described (Paris et al., Neurosci Lett, 1998), a significant interactive term by ANOVA was taken as evidence that both drug x and Aβ are modulating a common signal transduction pathway. However, if the effect of drug x and Aβ was simply additive (or subtractive), this suggested modulation of independent transduction pathways. Levene's test for equality of variance followed by t-test for independent samples was used for single mean comparisons. Alpha levels were set at 0.05 for all analyses. Analyses were performed using SPSS for Windows release 9.5.

RESULTS

Characteristics of Aβ vasoactivity

Figure 2:
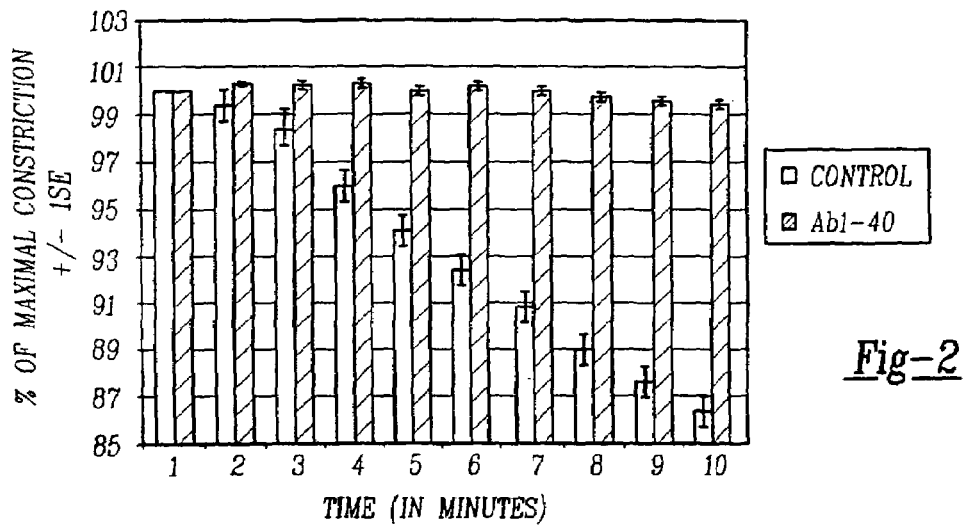
FIG. 2 is a bar graph illustrating that Aβ induces a long-lasting vasoconstriction.

It has previously been shown that freshly solubilized $A\beta_{1-40}$ or $A\beta_{1-42}$ increase the magnitude of constriction induced by ET-1 in isolated mammalian vessels, to a similar extent (Crawford et al., 1998). High levels of circulating $A\beta_{1-42}$ have been observed in AD patients, ranging from 30 to 150 nM (mean of approximately 50 nM), and this is approximately 6 times higher than the level of Aβ found in non-demented controls (Lambeau et al., 1994). Similar doses of freshly solubilized Aβ enhance ET-1-induced vasoconstriction (FIG. 1). Interestingly, Aβ does not only increase the magnitude of contraction induced by ET-1, but also enhances the sustained phase of ET-1-induced vasoconstriction (FIG. 2). As with freshly solubilized Aβ enhancement of ET-1-induced vasoconstriction, this sustained constriction event induced is observed with doses as low as 50 nM. Long-lasting vasoconstriction induced by Aβ is evident with other vasoconstrictors, such as phenylepherine or a thromboxane A2 analogue (U-46619), indicating that long-lasting vasoconstriction is not specific to the vasoconstrictor used.

More specifically, FIG. 1 shows the dose-response curve showing $A\beta_{1-40}$ vasoactivity. Certain aortic rings were treated with a dose range of $A\beta_{1-40}$ 5 minutes prior to the addition of a dose range of ET-1. Results are expressed as the mean ±1 SE of the percentage vasoconstriction increase over baseline. ANOVA revealed significant main effects of ET-1 dose (p<0.001), Aβ dose (p<0.001), and an interactive term between them (p<0.001). One-way ANOVA across ET-1 doses revealed significant between-groups differences (p<0.001), and post-hoc comparison across the 2.5 nM and 5 nM doses of ET-1 showed a significant difference between the 50 nM dose of Aβ and the Aβ-free condition (p=0.001).

FIG. 2 shows that Aβ induces a long-lasting vasoconstriction. Certain aortic rings were treated with 1 μM of $A\beta_{1-40}$ or untreated (control) 5 minutes prior to the addition of a dose range of ET-1 (1, 2.5, and 5 nM). Following the 5 nM dose of ET-1, maximum tension was taken as the t=0 time point [and standardized to 100% both in control (n=8) and Aβ-treated vessels (n=8)], with vasotension assessed for each following minute until t=10 minutes. ANOVA revealed significant main effects of Aβ (p<0.001), time (p<0.001), and an interaction between them (p<0.001). Post-hoc t test for independent samples across time points revealed a significant difference (p<0.001) between control and Aβ-treated rat aortae.

Effect of $PLA_2$ activation on Aβ vasoactivity

Figure 3:
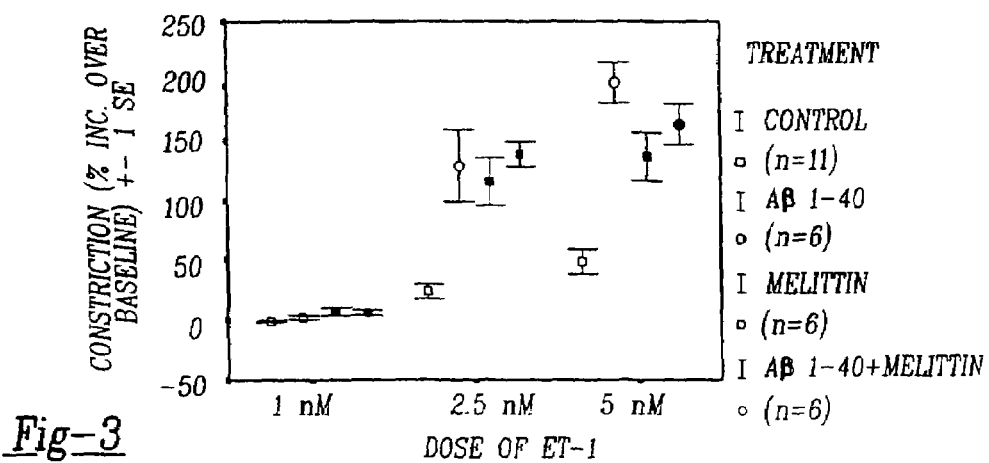
FIG. 3 is a graph showing the interaction among melittin, Aβ, and ET-1 on vasoconstriction.
Figure 4:
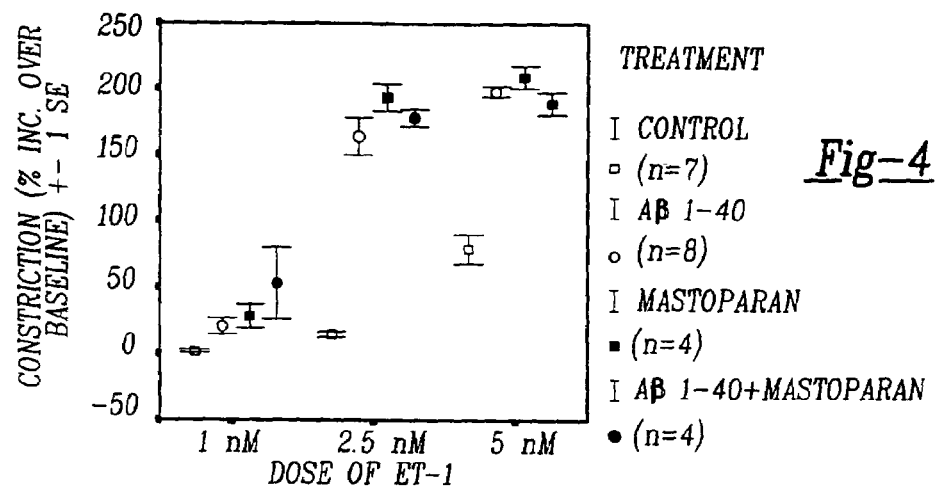
FIG. 4 is a graph showing the interaction among mastoparan, Aβ, and ET-1 on vasoconstriction.

Melittin (a constituent of bee venom) and mastoparan (a component of wasp venom) are two small peptides (26 and 14 amino acid residues, respectively) known to specifically activate $PLA_2$ and to stimulate G-proteins (preferentially $G_i$ and $G_o$; Gravitt et al., 1994; Kanemasa et al., 1992). Both of these peptides potentiate ET-1-induced vasoconstriction to a similar extent as Aβ, thus mimicking Aβ vasoactivity (FIGS. 3 and 4). Further, when either of these peptides are added to vessels in conjunction with ET-1 and Aβ, there is observed a 3-way interactive term by ANOVA, suggesting that Aβ and melittin or Aβ and mastoparan act on the same pathway leading to enhancement of ET-1-induced vasoconstriction.

Specifically, FIG. 3 shows the interaction among melittin, Aβ, and ET-1 on vasoconstriction. Certain aortic rings were treated with 1 μM of freshly solubilized $A\beta_{1-40}$, 1 μM of melittin, melittin+Aβ, or untreated (control) 5 minutes prior to the addition of a dose range of ET-1. ANOVA showed significant main effects of ET-1 dose (p<0.001), Aβ (p<0.001) and melittin (p<0.001), as well as significant interactive terms between ET-1 dose and either Aβ (p<0.001) or melittin (p<0.05). Furthermore, there was a significant interactive term among ET-1 dose, Aβ and melittin (p<0.01). One-way ANOVA across ET-1 doses revealed significant between-groups differences (p<0.001), and post-hoc testing showed significant differences between control and Aβ (p<0.001), control and melittin (p<0.02), and control and Aβ+melittin (p<0.01), but not between Aβ and melittin (p=0.776), or between Aβ and Aβ+melittin (p=0.989).

Also, FIG. 4 shows the interaction among mastoparan, Aβ, and ET-1 on vasoconstriction. Certain aortic rings were treated with 1 μM of freshly solubilized $A\beta_{1-40}$, 5 μM of mastoparan, mastoparan+Aβ, or untreated (control) 5 minutes prior to the addition of a dose range of ET-1. ANOVA showed significant main effects of ET-1 dose (p<0.001), Aβ (p<0.001) and mastoparan (p<0.001), as well as significant interactive terms between ET-1 dose and either Aβ (p=0.01) or mastoparan (p<0.001). There was also a significant interactive term among ET-1 dose, Aβ and mastoparan (p<0.001). One-way ANOVA across ET-1 doses revealed significant between-groups differences (p<0.001), and post-hoc testing showed significant differences between control and Aβ (p<0.001), control and mastoparan (p=0.001), and control and Aβ+mastoparan (p=0.001), but not between Aβ and mastoparan (p=0.940), or between Aβ and Aβ+mastoparan (p=0.973).

Effect of G-protein inhibition on Aβ vasoactivity

Figure 5:
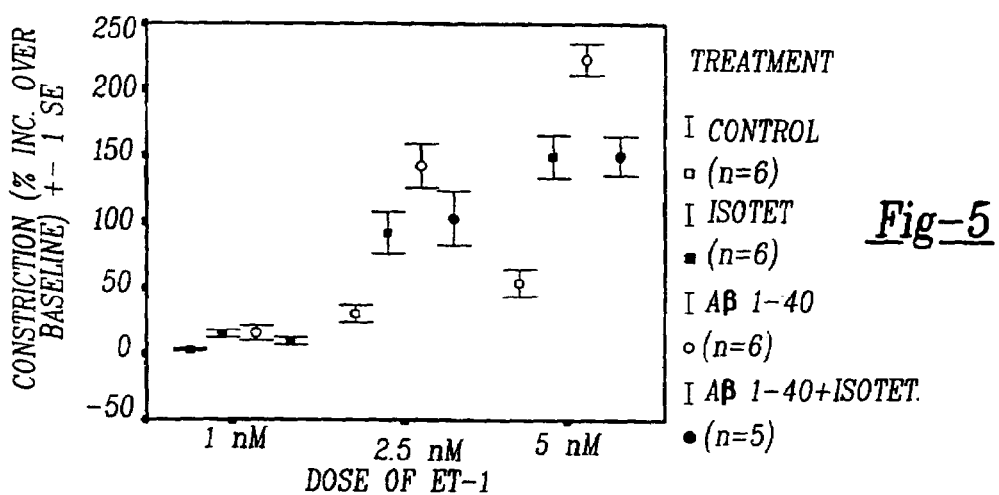
FIG. 5 is a graph showing the interaction among isotetrandrine, Aβ, and ET-1 on vasoconstriction.

Both melittin and mastoparan are known to be potent activators of G-proteins, mainly $G_i$ and $G_o$. The involvement of $G_o$ in Aβ vasoactivity was excluded, since the APP-derived peptide, APP657-676, a known stimulator of $G_o$ (Paris et al., 1998), was not able to modulate ET-1-induced vasoconstriction or to affect Aβ-vasoactivity. $G_i$ activation commonly results in an inhibition of adenylyl cyclase, and it has been shown that adenylyl cyclase does not mediate Aβ vasoactivity, since SQ-22536, a cell-permeable specific adenylyl cyclase inhibitor, does not have any effect on the vasoactive properties of Aβ (Rogers et al., 1993). Moreover, Aβ vasoactivity appears to be insensitive to pertussis toxin (PT), suggesting that it is independent of $G_i$. Interestingly, the activation of AA release induced by mastoparan is also completely insensitive to PT (Joyce-Brady et al., 1991), suggesting that mastoparan-induced $PLA_2$ activity occurs independently of $G_i$ activation, whereas inhibition of adenylyl cyclase by mastoparan is sensitive to PT. Isotetrandrine was also employed in the assay, which specifically inhibits G-protein activation of $PLA_2$, but not PLC or PLD (Walker et al., 1995). When added in combination with Aβ, isotetrandrine partially blocked Aβ vasoactivity (FIG. 5). Taken together, these data show that, while Aβ-vasoactivity is not significantly mediated via $G_i$ and $G_o$, it is dependent on the activation of the specific $PLA_2$-coupled G-protein. These data further substantiate the involvement of $PLA_2$s in the vasoactivity mediated by Aβ peptides.

FIG. 5 specifically shows the interaction among isotetrandrine, Aβ, and ET-1 on vasoconstriction. Certain aortic rings were treated with 1 μM of freshly solubilized $A\beta_{1-40}$, 25 μM of isotetrandrine (isotet.), isotetrandrine+Aβ, or untreated (control) 5 minutes prior to the addition of a dose range of ET-1. ANOVA showed significant main effects of ET-1 dose (p<0.001) and Aβ (p<0.001), but not for isotetrandrine (p=0.245). There were significant interactive terms between ET-1 dose and Aβ (p<0.001), and among ET-1 dose, Aβ and isotetrandrine (p<0.001). One-way ANOVA across ET-1 doses revealed significant between-groups differences (p<0.001), and post-hoc testing showed significant differences between control and Aβ (p<0.001), control and isotetrandrine (p=0.001), control and Aβ+isotetrandrine (p=0.001), between Aβ and isotetrandrine (p<0.05), but not between isotetrandrine and Aβ+isotetrandrine (p=0.994).

Figure 6:
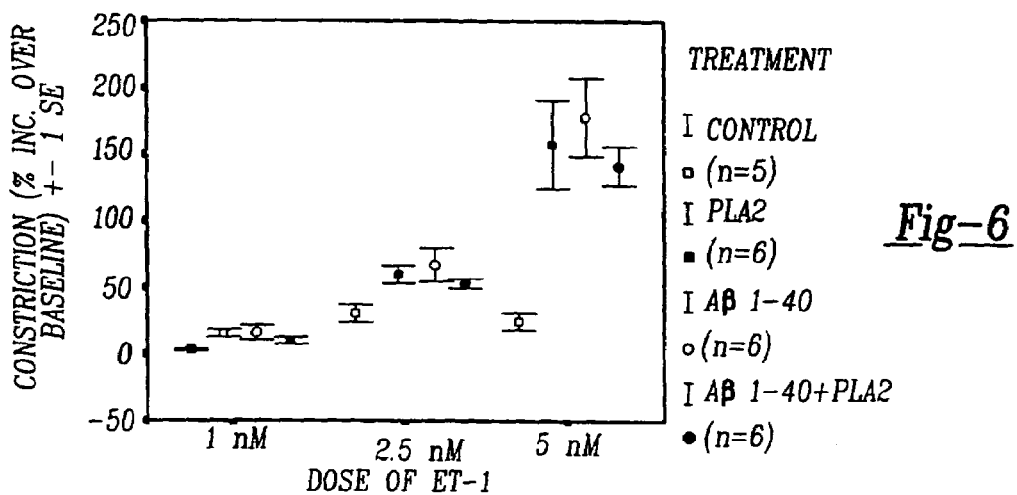
FIG. 6 is a graph showing the interaction among pancreatic $sPLA_2$ (type I), Aβ, and ET-1 on vasoconstriction.

Determination of the contribution of specific $PLA_2$ isoforms to Aβ vasoactivity In order to further substantiate the involvement of $PLA_2$ in Aβ vasoactivity, secretory porcine pancreatic $PLA_2$ (type I $sPLA_2$) was directly added into the vessel bath system. Porcine type I $sPLA_2$ displays a high homology compared to mammalian type I $sPLA_2$ isoforms, especially human type I $sPLA_2$ (Han et al., 1997). Similar to Aβ peptides, type I $sPLA_2$ does not display intrinsic vasoactive properties, but is able to enhance the vasoconstriction induced by ET-1, mimicking the vasoactivity of Aβ (FIG. 6). When added in combination with Aβ, there is observed an interactive term by ANOVA among ET-1, type I $sPLA_2$ and Aβ, suggesting that Aβ vasoactivity is mediated via stimulation of type I $sPLA_2$. Pretreatment of vessels with oleylox., a novel site-specific type I $sPLA_2$ inhibitor, completely blocks $Aβ_{1-40}$ (FIG. 7) and $Aβ_{1-42}$ vasoactivity. Moreover, there is observed statistical interaction among ET-1, Aβ (1-40 or 1-42), and oleylox., suggesting that activity of type I $sPLA_2$ is needed to bring about Aβ vasoactivity. The potential contribution of type II $sPLA_2$ to Aβ-induced vasoactivity was also explored by using quercetin, a selective inhibitor of type II $sPLA_2$ (Lue et al., 1996), and aristolochic acid, which preferentially inhibits activity of type II $sPLA_2$ over type I $sPLA_2$. Quercetin is unable to block Aβ vasoactivity, suggesting that type II $sPLA_2$ does not mediate Aβ-vasoactivity (FIG. 8). This is further substantiated by the fact that low doses of aristolochic acid (<10 μM) are unable to affect Aβ vasoactivity, whereas high doses (25 μM) result in the partial blockade of the vasoactive properties of Aβ.

Figure 9:
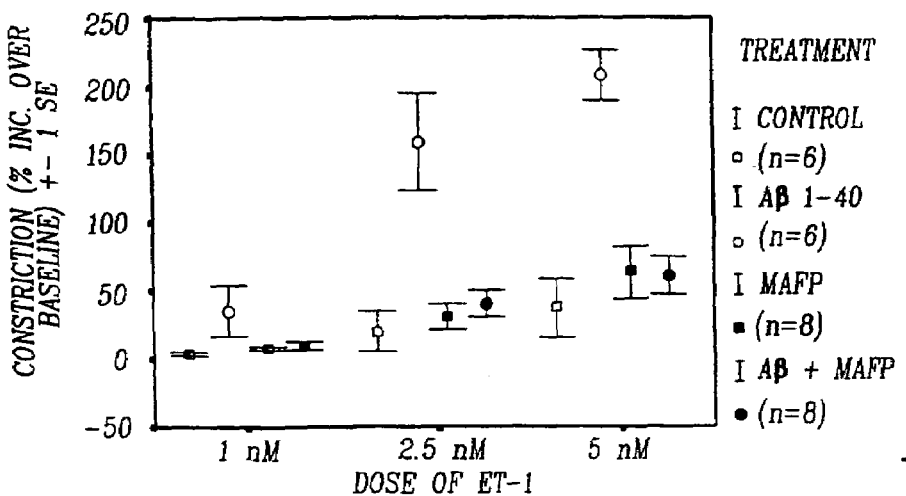
FIG. 9 is a graph showing the effect of $cPLA_2$ inhibition on Aβ induced vasoactivity.
Figure 10:
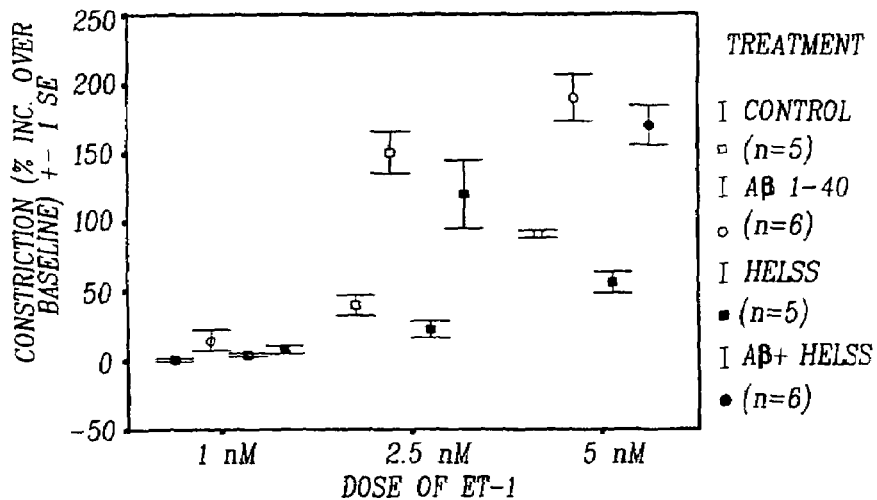
FIG. 10 is a graph showing the effect of $Ca_2$+-independent $PLA_2$ (type VI) inhibition on Aβ induced vasoactivity.

The possible involvement of cytosolic $PLA_2$ (type IV $cPLA_2$) in the vasoactive properties of Aβ was also investigated by using an irreversible inhibitor of $cPLA_2$, MAFP. Data show that MAFP completely inhibits Aβ-induced vasoactivity in a statistically interactive manner, demonstrating that $cPLA_2$ activity is required to mediate Aβ vasoactivity (FIG. 9). Furthermore, the contribution of calcium-independent $PLA_2$ (type VI) to the vasoactive properties of Aβ was investigated by incubating vessels with HELSS, a potent and irreversible inhibitor of type VI $PLA_2$. It was found that HELSS is unable to affect Aβ-induced vasoactivity, showing that type VI $PLA_2$ does not mediate the vasoactive properties of Aβ (FIG. 10). Collectively, these data show that the vasoactive effect exerted by Aβ is specifically mediated by type I $sPLA_2$ and type IV $cPLA_2$.

FIG. 6 shows the interaction among pancreatic $sPLA_2$ (type I), Aβ, and ET-1 on vasoconstriction. Certain aortic rings were treated with 1 μM of freshly solubilized $Aβ_{1-40}$, 1 U/mL of type I $sPLA_2$, $PLA_2$+Aβ, or untreated (control) 5 minutes prior to the addition of a dose range of ET-1. There were significant main effects by ANOVA of ET-1 dose (p<0.001), Aβ (p<0.001) and $PLA_2$ (p<0.01), as well as significant interactive terms between ET-1 dose and either Aβ (p<0.001) or $PLA_2$ (p<0.001). Furthermore, there was a significant interactive term among ET-1 dose, Aβ and $PLA_2$ (p<0.001). One-way ANOVA across ET-1 doses revealed significant between-groups differences (p<0.01), and post-hoc testing showed significant differences between control and Aβ (p<0.01), control and $PLA_2$ (p<0.02), and control and Aβ+$PLA_2$ (p<0.05), but not between Aβ and PLA2 (p=0.956), or between Aβ and Aβ+$PLA_2$ (p=0.807).

Figure 7:
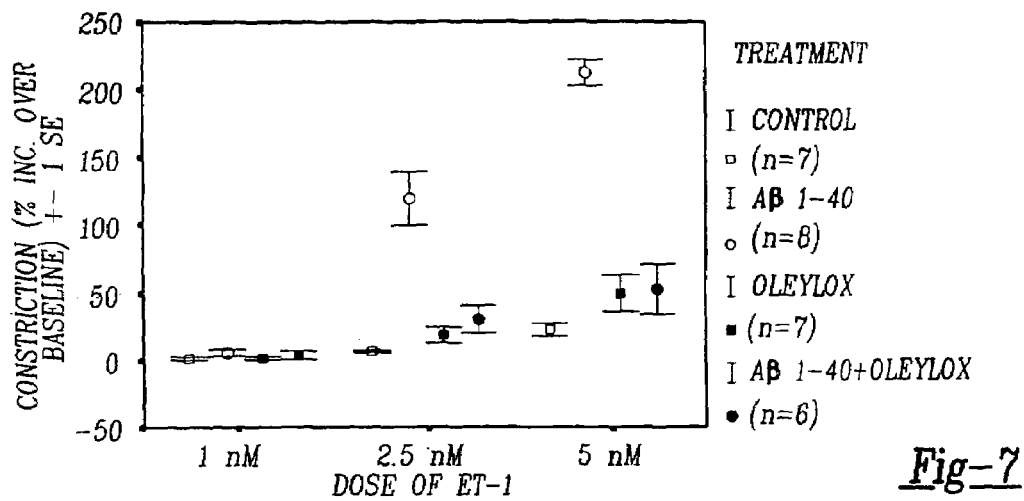
FIG. 7 is a graph showing the interaction among oleyloxyethylphosphocholine, $A\beta_{1-40}$, and ET-1 on vasoconstriction.
Figure 8:
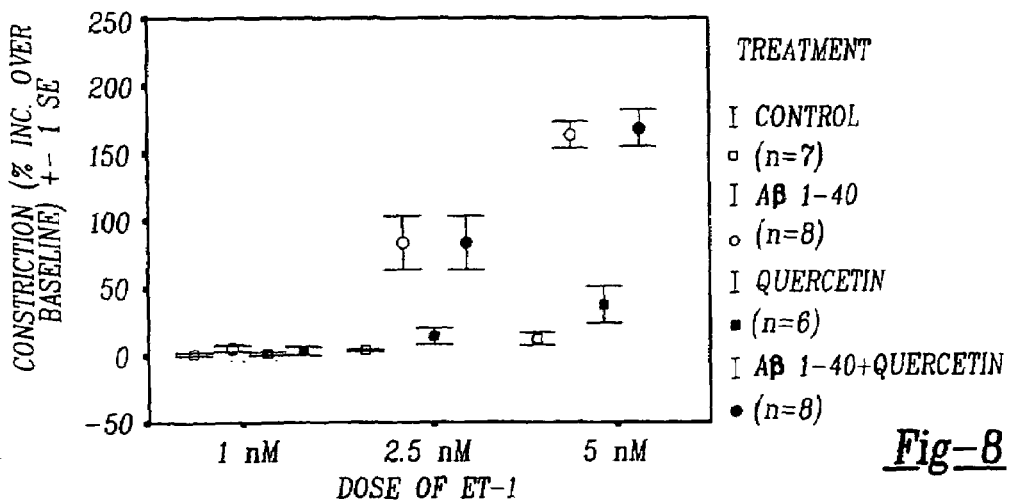
FIG. 8 is a graph showing the effect of $sPLA_2$ (type II) inhibition on Aβ induced vasoactivity.

Additionally, FIG. 7 shows the interaction among oleyloxyethylphosphocholine, $Aβ_{1-40}$, and ET-1 on vasoconstriction. Certain aortic rings were treated with 1 μM of freshly solubilized $Aβ_{1-40}$, 1 μM of oleylox., oleylox.+Aβ, or untreated (control) 5 minutes prior to the addition of a dose range of ET-1. There were significant main effects by ANOVA of ET-1 dose (p<0.001), Aβ (p<0.001), and of oleylox. (p<0.001). There were also significant interactive terms between ET-1 dose and either Aβ (p<0.001) or oleylox. (p<0.001), and among ET-1, Aβ and oleylox. (p<0.001). One-way ANOVA across ET-1 doses revealed significant between-groups differences (p<0.001), and post-hoc testing showed significant differences between control and Aβ (p<0.001), and Aβ and Aβ+oleylox. (p=0.001), but not between control and Aβ+oleylox. (p=0.756), control and oleylox. (p=0.886), or oleylox. and Aβ+oleylox. (p=0.992). Similar results were observed with $Aβ_{1-42}$.

FIG. 8 shows the effect of $sPLA_2$/(type II) inhibition on Aβ-induced vasoactivity. Certain aortic rings were treated with 1 μM of freshly solubilized $Aβ_{1-40}$, 10 μM of quercetin, quercetin +Aβ, or untreated (control) 5 minutes prior to the addition of a dose range of ET-1. There were significant main effects by ANOVA of ET-1 dose (p<0.001), Aβ (p<0.001), but not for quercetin (p=0.219). There was also a significant interactive term between ET-1 dose and Aβ (p<0.001), but not among ET-1, Aβ and quercetin (p=0.752). One-way ANOVA across ET-1 doses revealed significant between-groups differences (p<0.001), and post-hoc testing showed significant differences between control and Aβ (p=0.001), between control and Aβ+quercetin (p<0.001), between quercetin and Aβ+quercetin (p<0.01), but not between control and quercetin (p=0.919), or Aβ and Aβ+quercetin (p=0.999).

Also, FIG. 9 shows the effect of $cPLA_2$ inhibition on Aβ-induced vasoactivity. Certain aortic rings were treated with 1 μM of freshly solubilized $Aβ_{1-40}$, 1 μM of MAFP, MAFP+Aβ, or untreated (control) 5 minutes prior to the addition of a dose range of ET-1. There were significant main effects by ANOVA of ET-1 dose (p<0.001), Aβ (p<0.001), but not for MAFP (p<0.001). There were also significant interactive terms between ET-1 dose and Aβ (p<0.01), and among ET-1, Aβ and MAFP (p<0.01). One-way ANOVA across ET-1 doses revealed significant between-groups differences (p<0.001), and post-hoc testing showed significant differences between control and Aβ (p<0.001), and Aβ and Aβ+MAFP (p=0.001), but not between control and Aβ+MAFP (p=0.743), control and MAFP (p=0.868), or MAFP and Aβ+MAFP (p=0.994). Similar results were observed with $Aβ_{1-42}$.

FIG. 10 shows the effect of $Ca^{2+}$-independent $PLA_2$ (type VI) inhibition on Aβ-induced vasoactivity. Certain aortic rings were treated with 1 μM of freshly solubilized $Aβ_{1-40}$, 1 μM of HELSS, HELSS+Aβ, or untreated (control) 5 minutes prior to the addition of a dose range of ET-1. There were significant main effects by ANOVA of ET-1 dose (p<0.001), Aβ (p<0.001), but not for HELSS (p=0.01). There was also a significant interactive term between ET-1 dose and Aβ (p<0.001), but not among ET-1, Aβ and HELSS (p=0.661).

Contribution of arachidonic acid metabolism to Aβ vasoactivity

Figure 11:
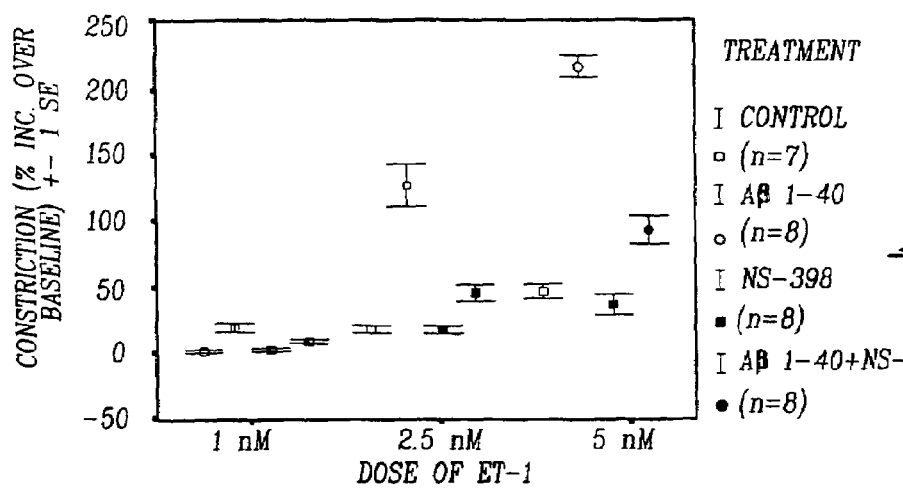
FIG. 11 is a graph showing the effect of COX-2 inhibition on Aβ enhancement of ET-1 induced vasoconstriction.

The data thus far had shown that Aβ mediates its vasoactive effect by activating specific $PLA_2$ isoforms. Activation of $cPLA_2$ results in the production of AA, since $cPLA_2$ displays strict substrate specificity for AA-containing phospholipids. AA is metabolized essentially through two distinct pathways, the COX pathway, which leads to the production of prostaglandins and thromboxanes, and the LOX pathway, which gives rise to leukotrienes and lipoxins. The effect of NS-398, a specific inhibitor of COX-2, on the vasoactivity mediated by Aβ was investigated first. It was observed that NS-398 is able to block Aβ vasoactivity in a statistically interactive manner, showing that Aβ enhancement of vasoconstriction is mediated through COX-2 (FIG. 11). The effect of MK-886, a compound which impairs the translocation of 5-LOX and its subsequent activation by 5-LOX activating protein, was then tested which showed that MK-886 also markedly inhibits Aβ vasoactivity in a statistically interactive manner, showing that Aβ-vasoactivity is mediated via the 5-LOX pathway. (FIG. 12).

Figure 13:
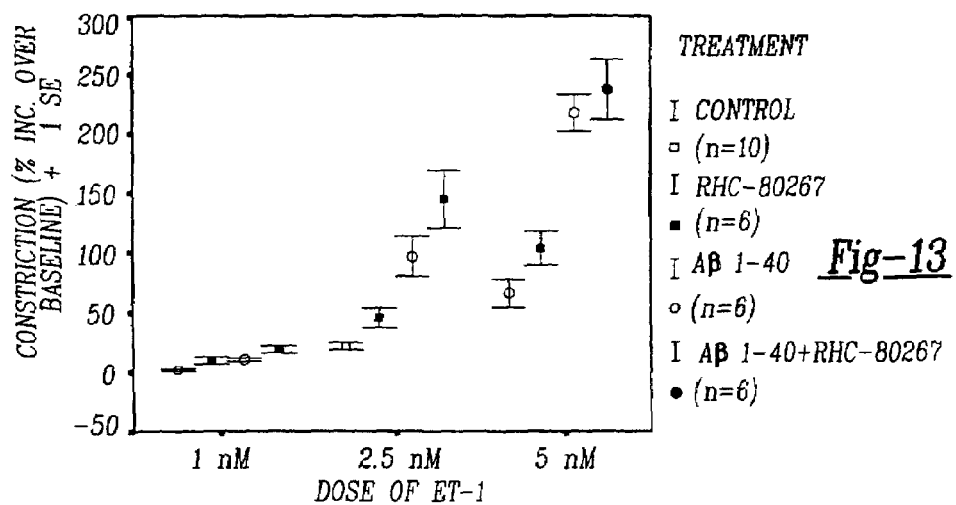
FIG. 13 is a graph showing the effect of RHC80267 on Aβ enhancement of ET-1 induced vasoconstriction.

AA can also be produced via diacylglygerol (DAG, a product of PLC) hydrolysis by DAG-lipase. A specific inhibitor of-DAG-lipase, RHC-80267, was used and this showed that DAG-lipase does not contribute to Aβ vasoactivity, since RHC-80267 is not able to modulate ET-1-induced vasoconstriction or to affect Aβ enhancement of ET-1-induced vasoconstriction (FIG. 13). However, treatment of vessels with DAG was able to potentiate ET-1-induced vasoconstriction, as well as Aβ enhancement of vasoconstriction, but this effect was merely additive (FIG. 14), suggesting that DAG does not impinge upon the Aβ pathway leading to vasoactivity. Since DAG is an endogenous stimulator of PKC, the data suggests that Aβ vasoactivity is PKC independent. To further substantiate this hypothesis, PKC was specifically inhibited by using bisindolylmaleimide I, and there was observed a statistically interactive reduction in ET-1-induced vasoconstriction, while reduction in Aβ vasoactivity was merely additive (FIG. 15). Taken together, these data demonstrate that Aβ vasoactivity is not mediated through PLC or PKC-associated pathways, and that stimulation of the $PLA_2$ pathway by Aβ is responsible for AA production which mediates Aβ vasoactivity.

Specifically, FIG. 11 shows the effect of COX-2 inhibition on Aβ-enhancement of ET-1-induced vasoconstriction. Certain aortic rings were treated with 1 µM of freshly solubilized Aβ$_{1-40}$, 5 µM of NS-398, NS-398 +Aβ, or untreated (control) 5 minutes prior to the addition of a dose range of ET-1. ANOVA revealed significant main effects of ET-1 dose ($p<0.001$), Aβ ($p<0.001$), and of NS-398 ($p<0.001$). There were also significant interactive terms between ET-1 dose and either Aβ ($p<0.001$) or NS-398 ($p<0.001$), and among ET-1 dose, Aβ and NS-398 ($p<0.001$). One-way ANOVA across ET-1 doses revealed significant between-groups differences ($p<0.001$), and post-hoc testing showed significant differences between control and Aβ ($p<0.001$), and Aβ and Aβ+NS-398 ($p=0.001$), but not between control and Aβ+NS-398 ($p=0.393$), control and NS-398 ($p=0.996$), or NS-398 and Aβ+NS-398 ($p=0.249$). Similar results were observed with Aβ$_{1-42}$.

Figure 12:
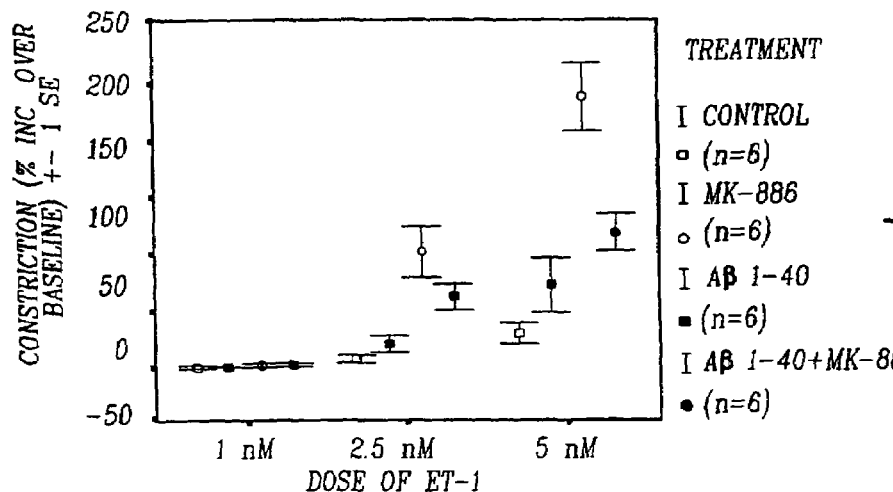
FIG. 12 is a graph showing the interaction among MK-886, and $A\beta_{1-40}$ and ET-1 on vasoconstriction.

Further, FIG. 12 shows the interaction among MK-886, Aβ$_{1-40}$ and ET-1 on vasoconstriction. Certain aortic rings were treated with 1 µM of freshly solubilized Aβ$_{1-40}$, 1 µM of MK-886, MK-886+Aβ, or untreated (control) 5 minutes prior to the addition of a dose range of ET-1. There were significant main effects by ANOVA of ET-1 dose ($p<0.001$), Aβ ($p<0.001$), and MK-886 ($p<0.05$). There was also a significant interaction between ET-1 dose and Aβ ($p<0.001$), and among ET-1 dose, Aβ, and MK-886 ($p=0.001$). However, an interaction between ET-1 dose and MK-886 ($p=0.159$) was noted. One-way ANOVA across the 2.5 and 5 nM doses of ET-1 revealed significant between-groups differences ($p<0.001$), and post-hoc testing showed significant differences between control and Aβ ($p<0.001$), Aβ and Aβ+MK-886 ($p<0.01$), and control and Aβ+MK-886 ($p<0.05$), but not between control and MK-886 ($p=0.639$), or MK-886 and Aβ+MK-886 ($p=0.286$). Similar results were observed with Aβ$_{1-42}$.

FIG. 13 shows the effect of RHC-80267 on Aβ-enhancement of ET-1-induced vasoconstriction. Certain aortic rings were treated with 1 µM of freshly solubilized Aβ$_{1-40}$, 8 µM of RHC-80267, RHC-80267 +Aβ, or untreated (control) 5 minutes prior to the addition of a dose range of ET-1. ANOVA revealed significant main effects of ET-1 dose ($p<0.001$), Aβ ($p<0.001$), and RHC-80267 ($p=0.001$). There was also a significant interactive term between ET-1 dose and Aβ ($p<0.001$), but not between ET-1 dose and RHC-80267 ($p=0.222$) or among ET-1 dose, Aβ and RHC-80267 ($p=0.482$).

Figure 14:
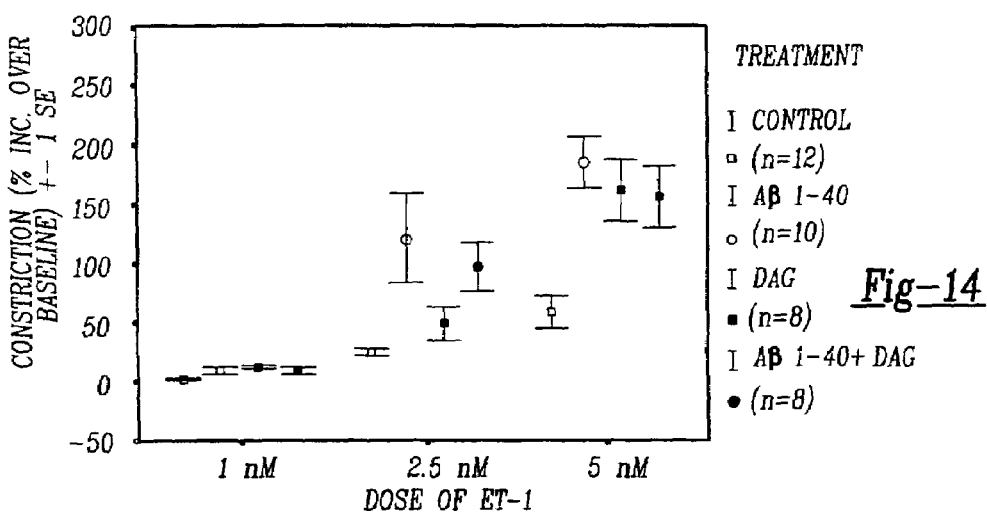
FIG. 14 is a graph showing the effect of DHE on Aβ enhancement of ET-1 induced vasoconstriction.
Figure 15:
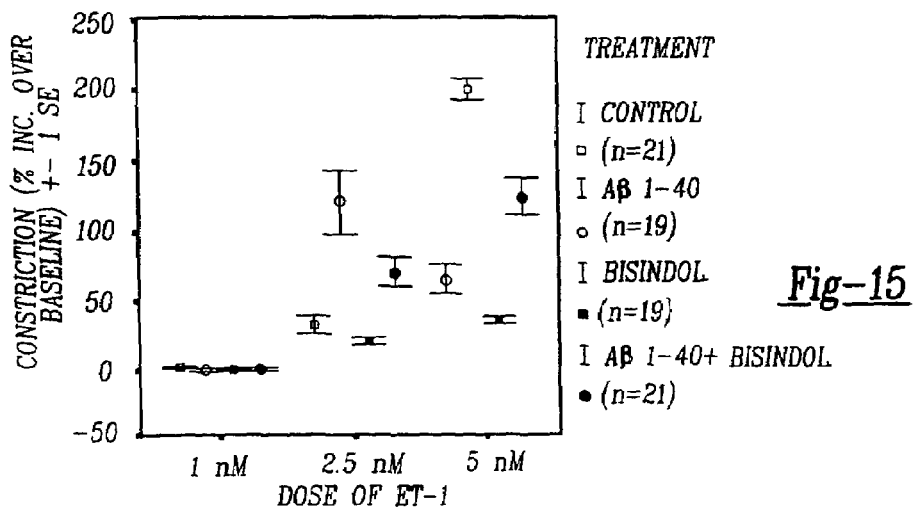
FIG. 15 is a graph showing the effect of bisindolylmaleimide I on Aβ enhancement of ET-1 induced vasoconstriction.

FIG. 14 shows the effect of DAG on Aβ-enhancement of ET-1-induced vasoconstriction. Certain aortic rings were treated with 1 µM of freshly solubilized Aβ$_{1-40}$, 10 µM of diacylglygerol (DAG), DAG+Aβ, or untreated (control) 5 minutes prior to the addition of a dose range of ET-1. ANOVA revealed significant main effects of ET-1 dose ($p<0.001$) and Aβ ($p<0.001$), but not DAG ($p=0.248$). There was also a significant interactive term between ET-1 dose and Aβ ($p<0.05$), but not between ET-1 dose and DAG ($p=0.397$) and not among ET-1 dose, Aβ and DAG ($p=0.123$).

FIG. 15 shows the effect of bisindolylmaleimide I on Aβ-enhancement of ET-1-induced vasoconstriction. Certain aortic rings were treated with 1 µM of freshly solubilized Aβ$_{1-40}$, 1.5 µM of bisindolylmaleimide I (bisindol.), bisindol. +Aβ, or untreated (control) 5 minutes prior to the addition of a dose range of ET-1. ANOVA revealed significant main effects of ET-1 dose ($p<0.001$), Aβ ($p<0.001$), but not of bisindol. ($p>0.05$). There were also significant interactive terms between ET-1 dose and either Aβ ($p<0.001$) or bisindol. ($p<0.001$), but not among ET-1 dose, Aβ and bisindol. ($p=0.184$).

Cross-talk between $sPLA_2$ and $cPLA_2$

Figure 16:
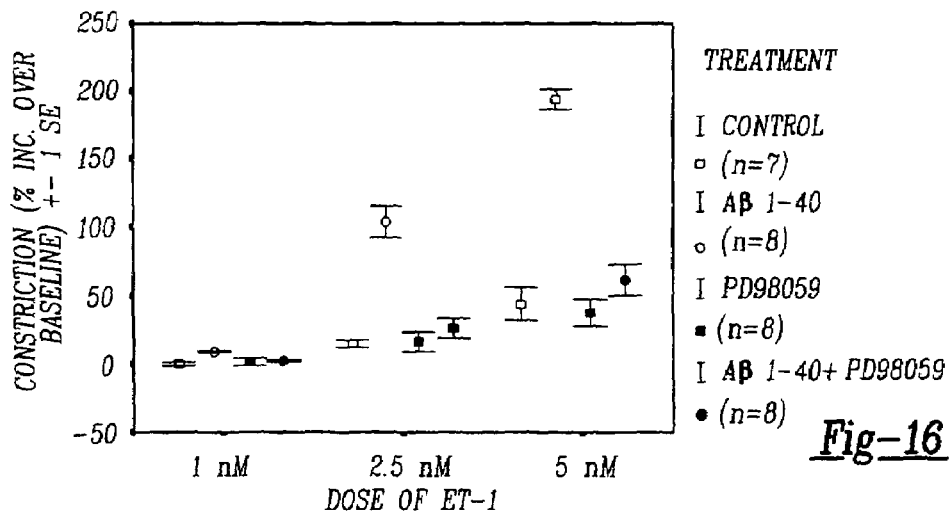
FIG. 16 is a graph showing the effect of MEK1/2 inhibition on $A\beta_{1-40}$ enhancement of ET-1 induced vasoconstriction.
Figure 17:
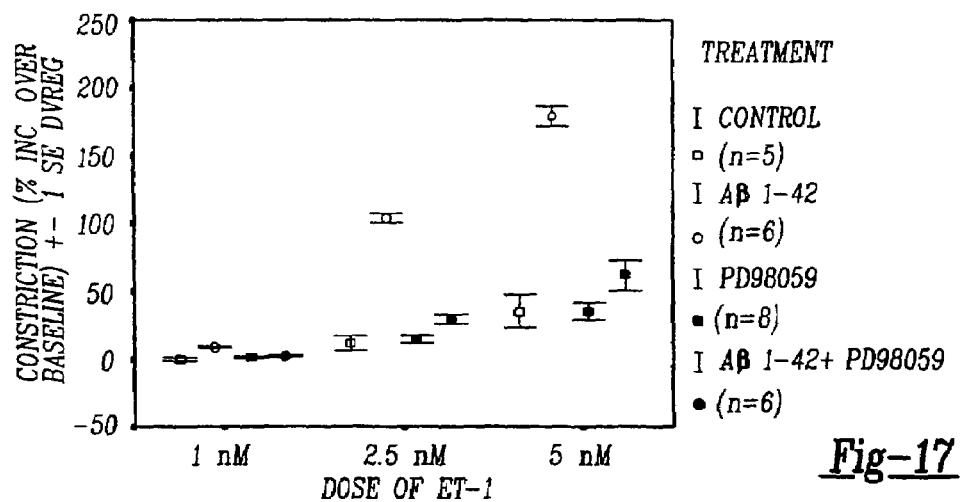
FIG. 17 is a graph showing the effect of MEK1/2 inhibition on $A\beta_{1-42}$ enhancement of ET-1 induced vasoconstriction.
Figure 18:
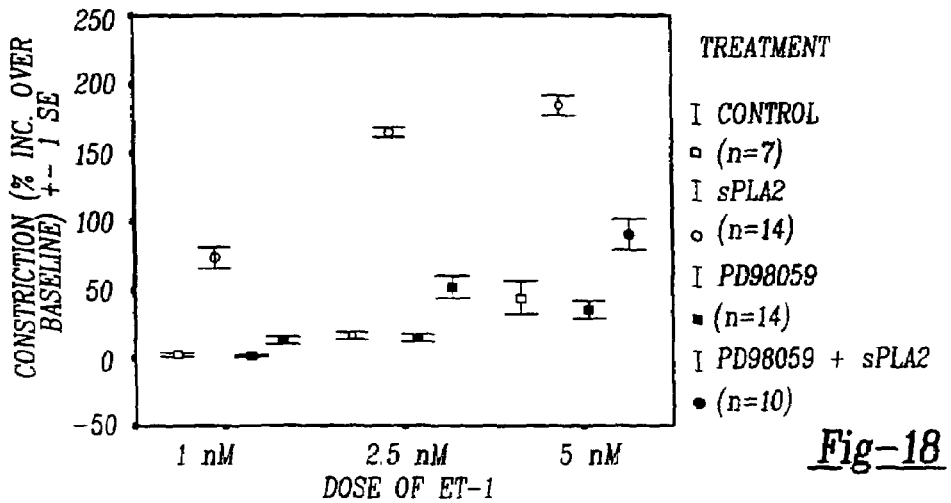
FIG. 18 is a graph showing the effect of MEK1/2 inhibition on $sPLA_2$ enhancement of ET-1 induced vasoconstriction.
Figure 19:
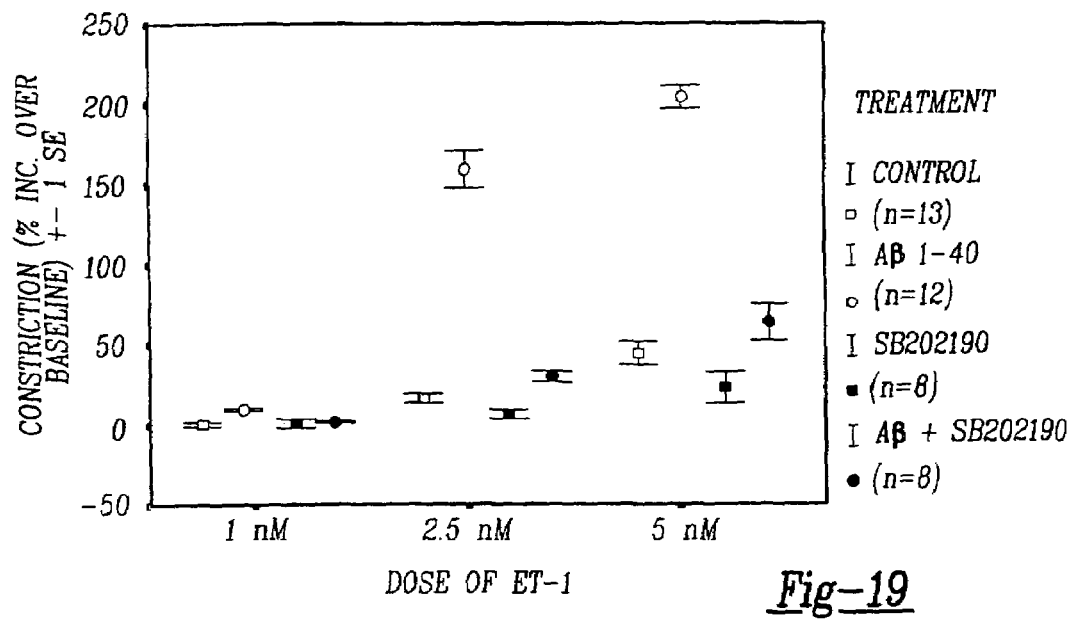
FIG. 19 is a graph showing the effect of p38MAPK inhibition on Aβ enhancement of ET-1 induced vasoconstriction.

Both $sPLA_2$ and $cPLA_2$ appeared to be necessary to mediate Aβ-vasoactivity from the data presented thus far, leaving the possibility open that cross-talk between these $PLA_2$s could be implicated in Aβ's vasoactivity. A complex network of interactions exists among the various $PLA_2$ isoforms. In particular, a functional cross-talk between type I $sPLA_2$ and $cPLA_2$, which is mediated by the MAPK module, has recently been demonstrated (Hernandez et al., 1998; Huwiler et al., 1997; Naidu et al., 1995). Thus, potential MAPK module-mediated cross-talk between these $PLA_2$s was investigated in the vessel bath system. Vessels were pre-treated with PD 98059, a highly specific MEK1/2 (MAPK kinase) inhibitor that has been shown to completely block $sPLA_2$-induced $cPLA_2$ activation (Huwiler et al., 1997). A complete blockade of Aβ$_{1-40}$ and Aβ$_{1-42}$ vasoactivity by PD 98059 was observed, showing that MEK1/2 activity is necessary to mediate Aβ vasoactivity (FIGS. 16 and 17). Interestingly, PD 98059 was also able to completely inhibit $sPLA_2$ enhancement of ET-1-induced vasoconstriction, showing that $sPLA_2$'s induction of vasoconstriction, like Aβ's, is essentially mediated via MEK1/2 (FIG. 18). Moreover, pretreatment of vessels with a specific inhibitor of p38 MAPK, SB 202190, resulted in complete inhibition of Aβ vasoactivity, further substantiating the involvement of the MAPK module in Aβ signaling (FIG. 19).

FIG. 16 shows the effect of MEK1/2 inhibition on Aβ$_{1-40}$-enhancement of ET-1-induced vasoconstriction. Certain aortic rings were treated with 1 µM of freshly solubilized Aβ$_{1-40}$, 25 µM of PD98059, PD98059 +Aβ, or untreated (control) 5 minutes prior to the addition of a dose range of ET-1. ANOVA revealed significant main effects of ET-1 dose ($p<0.001$), Aβ ($p<0.001$), and of PD98059 ($p<0.001$). There were also significant interactive terms between ET-1 dose and either Aβ (p<0.001) or PD98059 (p<0.001), and among ET-1 dose, Aβ and PD98059 (p<0.001). One-way ANOVA across ET-1 doses revealed significant between-groups differences (p<0.001), and post-hoc testing showed significant differences between control and Aβ (p<0.001), Aβ and Aβ+PD98059 (p<0.001) and control and Aβ+PD98059 (p<0.001), but not between control and PD98059 (p=1.00), or PD98059 and Aβ+PD98059 (p=0.880).

FIG. 17 shows the effect of MEK1/2 inhibition on $A\beta_{1-42}$-enhancement of ET-1-induced vasoconstriction. Certain aortic rings were treated with 1 μM of freshly solubilized $A\beta_{1-42}$, 25 μM of PD98059, PD98059+Aβ, or untreated (control) 5 minutes prior to the addition of a dose range of ET-1. ANOVA revealed significant main effects of ET-1 dose (p<0.001), Aβ (p<0.001), and of PD98059 (p<0.001). There were also significant interactive terms between ET-1 dose and either Aβ (p<0.001) or PD98059 (p<0.001), and among ET-1 dose, Aβ and PD98059 (p<0.001). One-way ANOVA across ET-1 doses revealed significant between-groups differences (p<0.001), and post-hoc testing showed significant differences between control and Aβ (p<0.001), Aβ and Aβ+PD98059 (p<0.001) and control and Aβ+PD98059 (p<0.001), but not between control and PD98059 (p=1.00), or PD98059 and Aβ+PD98059 (p=0.780).

FIG. 18 shows the effect of MEK1/2 inhibition on $sPLA_2$-enhancement of ET-1-induced vasoconstriction. Certain aortic rings were treated with 2.5 U/mL of sPLA, 25 μM of PD98059, PD98059+$sPLA_2$, or untreated (control) 5 minutes prior to the addition of a dose range of ET-1. ANOVA revealed significant main effects of ET-1 dose (p<0.001), PD98059 (p<0.001), and of $sPLA_2$ (p<0.001). There were also significant interactive terms between ET-1 dose and either $sPLA_2$ (p<0.001) or PD98059 (p=0.01), and among ET-1 dose, $sPLA_2$ and PD98059 (p<0.05). One-way ANOVA across ET-1 doses revealed significant between-groups differences (p<0.001), and post-hoc testing showed significant differences between control and $sPLA_2$ (p<0.001), $sPLA_2$ and $sPLA_2$+PD98059 (p<0.001), control and $sPLA_2$+PD98059 (p<0.05) and PD98059 and $sPLA_2$+PD98059 (p<0.01), but not between control and PD98059 (p=1.00).

Additionally, FIG. 19 shows the effect of p38 MAPK inhibition on Aβ-enhancement of ET-1-induced vasoconstriction. Certain aortic rings were treated with 1 μM of freshly solubilized $A\beta_{1-40}$, 5 μM of SB202190, SB202190+Aβ, or untreated (control) 5 minutes prior to the addition of a dose range of ET-1. ANOVA revealed significant main effects of ET-1 dose (p<0.001), Aβ (p<0.001), and of SB202190 (p<0.001). There were also significant interactive terms between ET-1 dose and either Aβ (p<0.001) or SB202190 (p<0.001), and among ET-1 dose, Aβ and SB202190 (p<0.001). One-way ANOVA across ET-1 doses revealed significant between-groups differences (p<0.001), and post-hoc testing showed significant differences between control and Aβ (p<0.001) and Aβ and Aβ+SB202190 (p<0.001), but not between control and Aβ+SB202190 (p=0.858), SB202190 and Aβ+SB202190 (p=0.519), or control and SB202190 (p=0.885). Similar results were observed with $A\beta_{1-42}$.

Modulation of [$^3$H] AA release by Aβ in rat aortae

Figure 20:
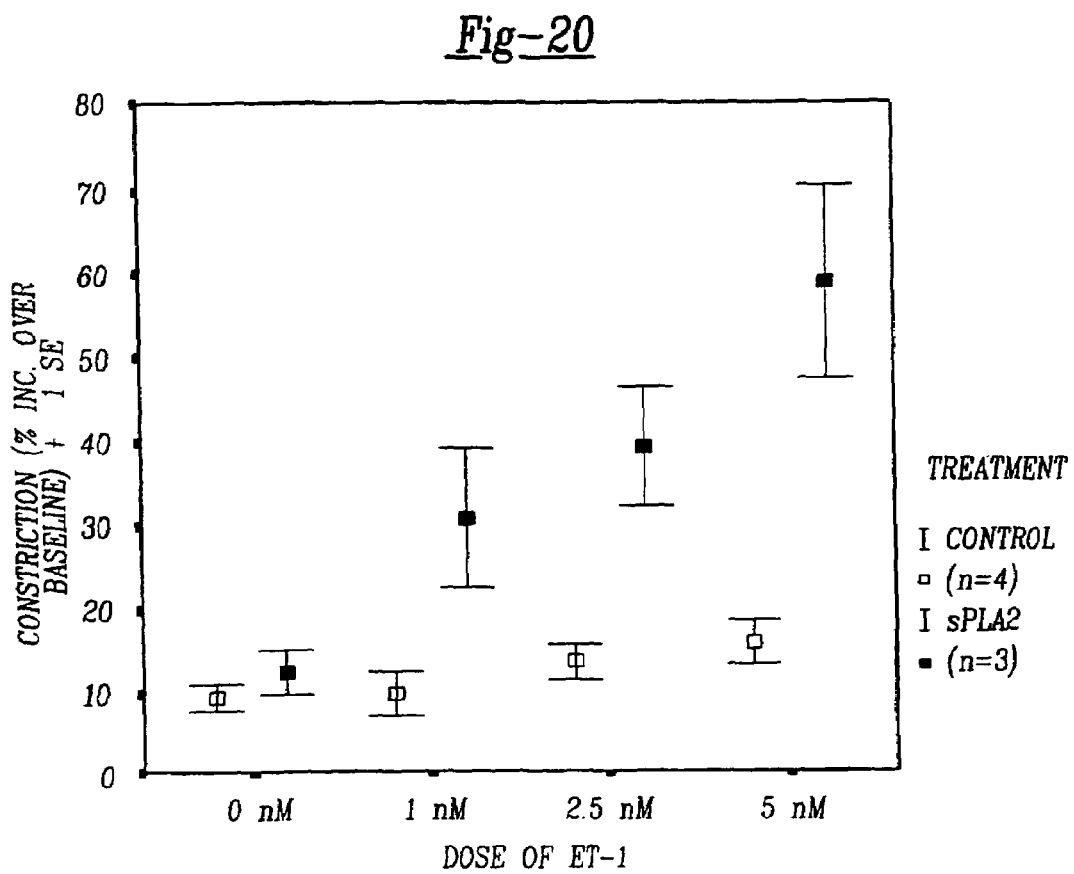
FIG. 20 is a graph showing the effect of $sPLA_2$ on [$^3$H]AA release.
Figure 21:
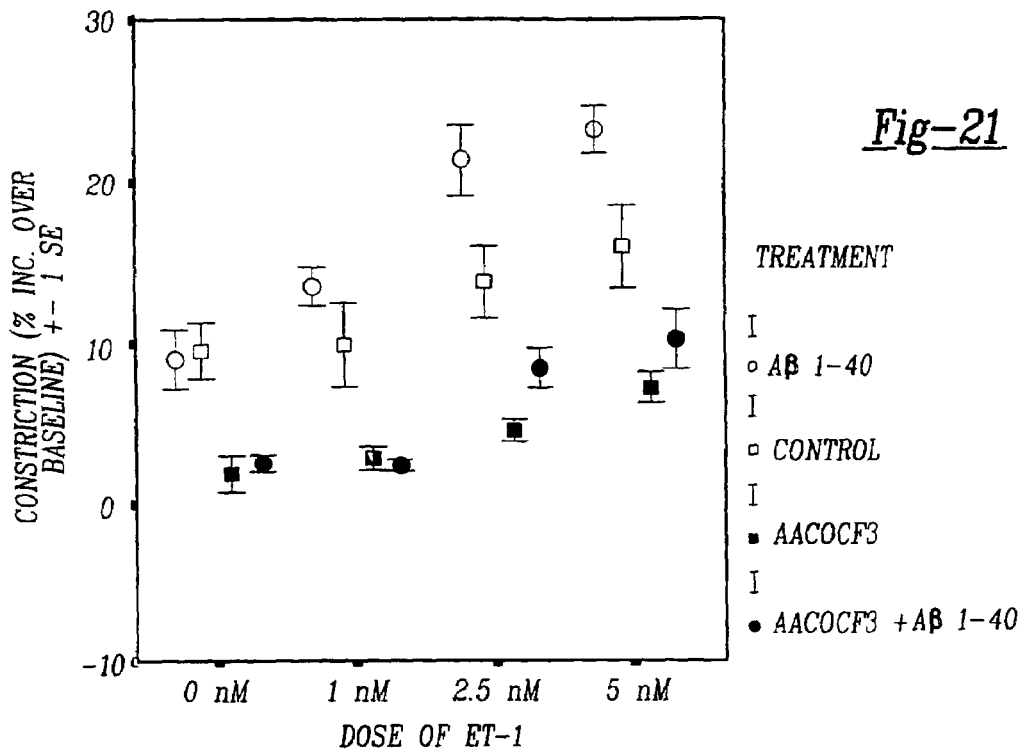
FIG. 21 is a graph showing the effect of $cPLA_2$ inhibition on [$^3$H]AA release by Aβ.

Since the data suggested that Aβ vasoactivity was mediated by activation of $PLA_2$, the ability to stimulate the release of AA from intact aortic rings was investigated. As previously described, activation of $PLA_2$ can be detected by pre-incubating cells or intact rat aortae with [$^3$H]AA and measuring [$^3$H]AA release (Naidu et al., 1995). FIG. 20 shows that treatment of aortic rings with $sPLA_2$ results in an increased release of [$^3$H]AA, confirming the validity of such an experiment to detect elevated [$^3$H]AA release in response to increased $PLA_2$ activity. It has been observed that Aβ enhances the release of [$^3$H]AA from aortic rings in comparison to controls rings, further substantiating that Aβ stimulates $PLA_2$ activity (FIG. 21). Moreover, this increase in [$^3$H]AA induced by Ab is inhibited by co-treating vessels with AACOCF3, a specific $cPLA_2$ inhibitor, showing that $cPLA_2$ mediates the release of AA induced by Aβ (see FIG. 21). Aβ-induced [$^3$H]AA release is also blocked by PD98059 (FIG. 22), confirming the requirement of MEK1/2 activity for Aβ-induced stimulation of $cPLA_2$. Taken together, these data further demonstrate that Aβ induces activation of $cPLA_2$ via stimulation of MEK1/2.

FIG. 20 shows the effect of $sPLA_2$ on [$^3$H]AA release. Intact aortic rings were incubated with [$^3$H]AA in PSS for 24 hours at 4° C. Unincorporated [$^3$H]AA was removed by multiple washes in Kreb's buffer, and then aortic rings were preincubated in the vessel bath system for 5 minutes with 10 U/mL of $sPLA_2$ or untreated (control) prior to treatment with a dose range of ET-1. ANOVA revealed significant main effects of ET-1 dose (p<0.001) and sPLA2 (p<0.001). Post-hoc t-test for independent samples revealed a significant difference (p<0.001) between control and Aβ-treated vessels across the 1 nM to 5 nM ET-1 dose range.

Specifically, FIG. 21 shows the effect of $cPLA_2$ inhibition on [$^3$H]AA release induced by Aβ. Intact aortic rings were incubated with [$^3$H]AA in PSS for 24 hours at 4° C. Unincorporated [$^3$H]AA was removed by multiple washes in Kreb's buffer, and then aortic rings were preincubated in the vessel bath system for 5 minutes with $A\beta_{1-40}$ (1 μM), AACOCF3 (1 μM), $A\beta_{1-40}$ +AACOCF3, or untreated (control) prior to treatment with a dose range of ET-1. ANOVA revealed significant main effects of ET-1 dose (p<0.001), Aβ (p<0.001), and AACOCF3 (p<0.001). One-way ANOVA including the 1 nM to 5 nM ET-1 doses showed significant between-groups differences (p<0.001), and post-hoc testing showed significant differences between control and Aβ (p<0.01), control and AACOCF3 (p<0.001), and between Aβ and AACOCF3 +Aβ (p<0.001).

Figure 22:
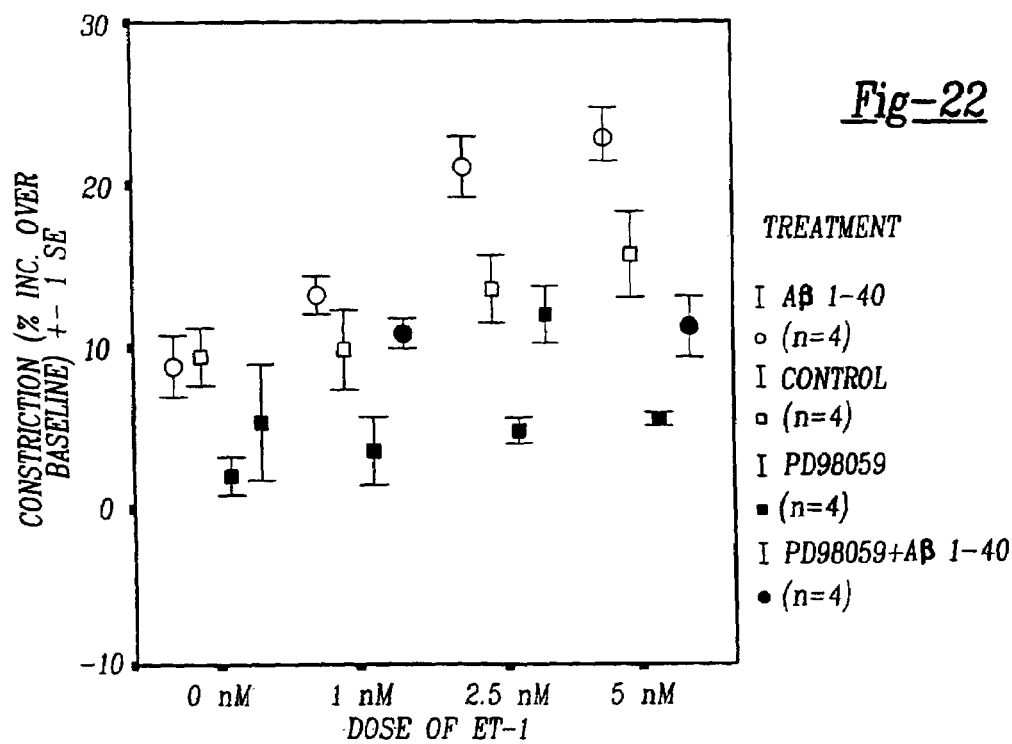
FIG. 22 is a graph showing the effect of MEK1/2 inhibition on [$^3$H]AA release induced by Aβ.

FIG. 22 shows the effect of MEK1/2 inhibition on [$^3$H]AA release induced by Aβ. Intact aortic rings were incubated with [$^3$H]AA in PSS for 24 hours at 4° C. Unincorporated [$^3$H]AA was removed by multiple washes in Kreb's buffer, and then aortic rings were preincubated in the vessel bath system for 5 minutes with $A\beta_{1-40}$ (1 μM), PD98059 (25 μM), $A\beta_{1-40}$ +PD98059, or untreated (control) prior to treatment with a dose range of ET-1. ANOVA revealed significant main effects of ET-1 dose (p<0.001), Aβ (p<0.001), and PD98059 (p<0.001). One-way ANOVA including the 1 nM to 5 nM ET-1 doses showed significant between-groups differences (p<0.001), and post-hoc testing showed significant differences between control and Aβ (p<0.01), control and PD98059 (p<0.01), and between Aβ and PD98059 +Aβ (p<0.01).

Discussion

Vascular pathology is the norm in advanced cases of AD, with cerebral amyloid angiopathy (CAA) being one of the commonest abnormalities detected at autopsy in carefully standardized examination (83% of AD cases as assessed by CERAD; 12). It has been shown that soluble Aβ peptides display vasoactive properties; specifically, they are able to enhance the magnitude of contraction induced by ET-1 (Crawford et al., 1998; Paris et al., 1998), and to oppose the relaxation induced by acetylcholine (Tischfield, J. A., 1997) or nitric oxide (Rogers et al., 1993). In addition, rats intra-arterially infused with freshly solublized Aβ exhibit decreased cerebral blood flow (Thomas et al., 1996), and transgenic mice which overproduce Aβ peptides display enhanced cerebrovascular constriction and resistance to relaxation in response to exogenous application of vasoconstrictors and vasorelaxants, respectively (Iadecola et al., 1999).

These data suggest that, in life, elevated levels of circulating Aβ may have similar effects on the peripheral and cerebral vasculature. At the clinical level, the possibility arises that this effect of soluble Aβ contributes to hypoperfusion and perhaps ischaemia in AD brains, thereby amplyfying the AD pathological process. With regard to hypoperfusion, both SPECT and PET studies confirm reduction in cerebral blood flow in AD (Duara et al., 1986; Johnson et al., 1987). As a first step to elucidating the contribution of Aβ to the vascular pathology associated with AD, the focus was placed on determining how Aβ-mediates its vasoactive effects.

Several converging lines of evidence suggest that Aβ peptides and inflammation may be linked in the pathogenesis of AD. For example, senile plaques observed in AD are sites of classical inflammatory processes, as evidenced by the presence of numerous degenerating neurons, reactive microglia and astrocytes, cytokines, and complement proteins (Itagaki et al., 1989; Minami et al., 1993; Wisniewski et al., 1993). In addition, cPLA$_2$ immunoreactivity has been shown to be increased in AD brains, specifically in reactive astrocytes in regions that contain numerous Aβ deposits (Stewart et al., 1997), suggesting a potential association between cPLA$_2$ and AD pathology. Furthermore, reactive glia are frequently co-localized with cerebral microvessels in AD brains (Wisniewski et al., 1992; Zhu et al., 1998), suggesting that the vasculature may be a site of inflammatory processes. Based on such evidence, the possible relationship between the vasoactive properties of Aβ and inflammation was investigated.

Aβ vasoactivity is mediated by a pro-inflammatory pathway, the PLA$_2$ cascade, which plays a role in signal transduction by allowing the production of bioactive lipids (Dennis et al., 1991; Sisoda et al., 1995). The results show that the vasoactive properties of Aβ are specifically mediated by type I sPLA$_2$ and cPLA$_2$, but not by type II sPLA$_2$ or type VI calcium-independent PLA$_2$. Type I sPLA$_2$ is abundant in pancreatic juice in many mammals, and thus is frequently referred to as pancreatic sPLA$_2$, and was originally thought to be involved in digestion of glycerophospholipids in nutrients. However, increased levels of type I sPLA$_2$ mRNA and protein are produced by non-digestive cells, where it may act as a regulator of cellular functions via the sPLA$_2$ receptor (sPLA$_2$-R), or via the direct release of bioactive fatty acids (Lehtonen et al., 1996; Itagaki et al., 1989; Tsunoda et al., 1995).

The data show that inhibition of either type I sPLA$_2$ or cPLA$_2$ is sufficient to block Aβ vasoactivity, suggesting that these two enzymes act in concert to bring about Aβ vasoactivity. This idea is supported by the existence of a sophisticated network of interactions (cross-talk) between various PLA$_2$s. Interestingly, it has been shown that the products of sPLA$_2$'s catalytic action, specifically lysophosphatidylcholine, lysophosphatidic acid and cis-unsaturated fatty acids (including arachidonic acid), activate PKC and the classical MAPK module (including Raf-1 kinase, MEK and the p44/42 and p38 isoforms of MAPK).

Ultimately, sPLA$_2$s catalytic action has been shown to phosphorylate and activate cPLA$_2$ via PKC, p42/p44 or p38 MAPK in various cell systems (Hernandez et al., 1998; Husain et al., 1998; Huwiler et al., 1997; Kan et al., 1996). In order to determine which kinases were responsible for sPLA$_2$-cPLA$_2$ cross-talk in the system, the effect of PKC modulation was first evaluated. Both DAG, an endogenous stimulator of PKC, and bisindolylmaleimide I, a specific inhibitor of PKC, were able to enhance and reduce Aβ vasoactivity, respectively. Yet, these effects were merely additive (no interaction was noted by ANOVA), showing that PKC does not provide for sPLA$_2$-cPLA$_2$ cross-talk to ensure Aβ vasoactivity. Since metabolism of DAG by DAG-lipase leads to AA production independently of the PLA$_2$ system, the effect of a specific inhibitor of DAG-lipase, RHC-80267, was assessed and it was found that this compound fails to block Aβ vasoactivity, showing that neither DAG-lipase nor the DAG-derived AA mediates Aβ vasoactivity. Because DAG is a product of phospholipase C (PLC), these data also suggest that Aβ vasoactivity is PLC-independent. Moreover, propanolol, which has been shown to inhibit PLD, is unable to block Aβ vasoactivity.

In order to determine if the cross-talk between type I sPLA$_2$ and type IV cPLA$_2$ was mediated by the MAPK module in the system, rat aortae were pre-incubated with PD 98059 or SB 202190, which block the activity of MEK1/2 (resulting in blockade of downstream p42/p44 MAPK, Dudley et al., 1995) or p38 MAPK, respectively. PD 98059 and SB 202190 have also been shown to inhibit the phosphorylation and activation of type IV cPLA$_2$ (Borsch-Haubold et al., 1998; Hernandez et al., 1998; Husain et al., 1998; Huwiler et al., 1997). PD 98059 completely abolished Aβ vasoactivity as well as Aβ-induced [$^3$H]AA release, showing that MEK1/2 activation is required to insure functional sPLA$_2$-cPLA$_2$ cross-talk which mediates Aβ vasoactivity. SB 202190 addition also resulted in blockade of Aβ vasoactivity, supporting the requirement of p38 MAPK in promotion of this effect. Since stimulation of the MAPK module results in cPLA2 activation, the contribution of cPLA$_2$ to Aβ's bioactivity was assessed. Cytosolic PLA$_2$ inhibition (by MAFP or AACOCF3) also blocked both Aβ vasoactivity and Aβ-induced [$^3$H]AA release from rat aortae.

Several studies have demonstrated that a variety of biological responses induced by type I sPLA$_2$ are mediated via sPLA$_2$-R, including cell proliferation (Arita et al., 1991), progression of endotoxic shock (Hanasaki et al., 1997), cell invasion (Kundu et al, 1997), chemokinesis (Kanemasa et al., 1992), eicosanoid production (Kishino et al., 1994; Tohkin et al., 1993), airway and vascular smooth muscle contraction (Kanemasa et al., 1992; Nitsch et al., 1992), and fertilization (Okamoto et al., 1995).

The sPLA$_2$-R has sequence homologies to the macrophage mannose receptor, a membrane protein involved in the endocytosis of glycoproteins. The short cytoplasmic tail of the sPLA$_2$-R does not display any characteristic sequence motif that could be responsible for coupling to known signaling pathways. However, it has been suggested that sPLA$_2$, independently of its catalytic action, can activate cPLA$_2$ on a human astrocytoma cell line via a mechanism involving sPLA$_2$-R, since an antagonist of this receptor, p-aminophenyl-α-D-mannopyranoside-bovine serum albumin (mannose-BSA) blocks cPLA$_2$ activation induced by sPLA$_2$ (Hernandez et al., 1998). The effect of sPLA2-R blockade was investigated using mannose-BSA. A statistical interaction among mannose-BSA, Aβ and ET-1 was noted but does not allow the conclusion that a stimulation of the sPLA$_2$-R may contribute to Aβ vasoactivity, since mannose-BSA was vasoactive to a similar extent as Aβ in the assay. Moreover, inactivation of sPLA$_2$ with dithiothreithol or oleyloxyphosphocholine, which does not block the binding of sPLA$_2$ to its receptor, results in the inhibition of sPLA$_2$-induced vasoconstriction, showing that the sPLA$_2$-R is not required for sPLA$_2$-induced vasoactivity. These data further suggest that the cross-talk between sPLA$_2$ and cPLA$_2$, which results in Aβ vasoactivity, is not significantly affected by the sPLA$_2$-R, but is promoted by a product of sPLA$_2$.

Since cPLA$_2$ displays a strict substrate specificity for AA-containing phospholipids, the Aβ-induced cPLA$_2$ signaling pathway will result in an increase in production of AA, and thus a possible enhancement of eicosanoids via COXs and LOXs. It was observed that AA can enhance ET-1-induced constriction and also noted a statistical interaction among Aβ, AA and ET-1, showing that AA mediates Aβ vasoactivity. It was also shown that Aβ results in an increased release of [$^3$H]AA in the system, providing for two possibilities; either AA is directly effecting Aβ vasoactivity, or downstream eicosanoid products of AA are responsible. NS-398, a specific inhibitor of COX-2 (Futaki et al., 1994), was able to block Aβ vasoactivity. Moreover, MK-886, a specific inhibitor of the 5-LOX activating protein (which allows for translocation of 5-LOX to the membrane and its subsequent activation; Abramovitz et al., 1993), was also able to block Aβ vasoactivity, demonstrating the requirement of 5-LOX for Aβ signaling. Interestingly, simultaneous COX-2 and 5-LOX inhibition resulted in the complete blockade of Aβ vasoactivity, confirming that both COX-2 and 5-LOX cooperatively mediate Aβ vasoactivity.

Therefore, the initiating event leading to Aβ vasoactivity is a stimulation of type I sPLA$_2$ activity followed by activation of p44/42 and p38 MAPKs, which will induce cPLA$_2$ phosphorylation, leading to its activation and ultimately to the production of AA. Finally, downstream of AA production, 5-LOX and COX-2 can mediate Aβ vasoactivity via multiple eicosanoid endproducts. Aβ can induce the release of leukotriene B4, a stable eicosanoid product of 5-LOX, from microglia, showing that Aβ stimulates a common signal transduction pathway in different cell types (Rogers et al., 1993). In cell-free experiments, Aβ peptides have been shown to induce type I sPLA$_2$ activity (Lin et al., 1993). Furthermore, there is considerable evidence for an abnormal phospholipid metabolism in AD patients, as mentioned previously. Such evidence points principally to increased degradation of membrane phospholipids in AD brains, where marked increases have been reported in the levels of prostaglandins and lipid peroxides (Iwamoto et al., 1989), both products of PLA$_2$ activity.

Taken together, the data show that Aβ vasoactivity is mediated by a pro-inflammatory response, showing a link between AD-type vascular pathology and inflammation. Although it is generally regarded that aggregated and fibrillar Aβ deposits in amyloid plaques can trigger inflammation, soluble forms of the peptide have not been previously investigated in relation to inflammation.

Example 2

The following example serves to illustrate that the sPLA2/AA/5-LOX/COX-2 pathway is also activated by soluble Aβ peptides in microglia, providing for an additional system where Aβ peptides stimulate this pathway. Additionally, this example illustrates that substances which inhibit this pathway block the effect of Aβ in microglia.

Methods

Leukotriene -B4 (LTB4) enzyme-linked immunoabsorbant assay (ELISA). Quantitative determination of LTB4 levels was made using a competitive binding ELISA (R&D Systems, Minneapolis, Minn.) designed to measure LTB4 in cell culture supernatants (as described in Paris et al., Exp Neurol 1999). A murine microglial cell line (N9) was provided by Dr. Paola Ricciardi-Castagnoli (Cellular Pharmacology Center, Milan, Italy) and were grown in RPMI medium supplemented with five percent fetal calf serum, 2 mM glutamine, 100 U/mL penicillin, 0.1 μg/mL streptomycin and 0.05 mM 2-mercaptoethanol. Microglial cells were seeded at 50,000 cells/well in 6-well plates (Falcon, France) and treated with Aβ$_{1-40}$ (500 nM), drugs which oppose the PLA2/AA/5-LOX/COX-2 pathway, or untreated (control) and incubated for 18 hours. Cell supernatants were then collected and diluted 10-fold in assay buffer. 50 μL of diluted samples were then used in the assay, and each sample was assayed in duplicate. Manipulations were performed in accordance with the manufacturer's instruction. A spectramax 250 spectrophotometer (Molecular Devices, San Diego, USA) was used to measure absorbance at 405 nm and a standard curve was plotted using a 4-parameter model.

Measurement of [$^3$H]AA release in cultured cells. Microglial cells were cultured as described above, seeded at 50,000 cells/well in 6-well plates (Falcon, France), and incubated with 0.4 μCi/mL [$^3$H]AA for 18 h. Cells were washed multiple times with 1 mL of complete medium and were then treated with 1 μM of Aβ$_{1-40}$ or 10 U/mL of sPLA2 for 5 h. Cell culture supernatants were collected each hour following treatment and radioactivity was quantified as described above.

Statistical analysis. Analysis of variance (ANOVA) was used to analyze the data, with post-hoc comparisons of means carried out where appropriate by Sheffe's or Bonferonni's methods. As previously described (Paris et al., Neurosci Lett, 1998), a significant interactive term by ANOVA was taken as evidence that both drug x and Aβ are modulating a common signal transduction pathway. However, if the effect of drug x and Aβ was simply additive (or subtractive), this suggested modulation of independent transduction pathways. Levene's test for equality of variance followed by t-test for independent samples was used for single mean comparisons. Alpha levels were set at 0.05 for all analyses. Analyses were performed using SPSS for Windows release 9.5.

Results and Discussion

Figure 23:
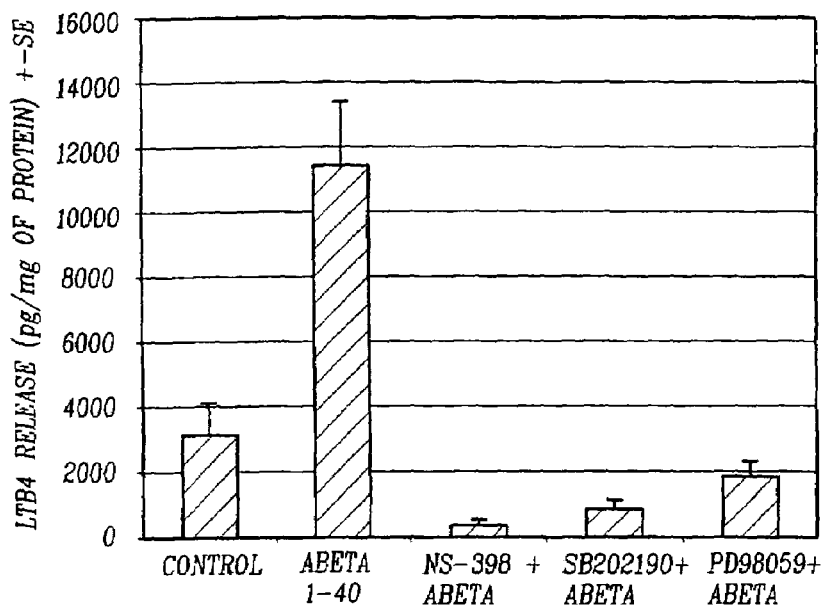
FIG. 23 is a graph showing that Aβ-induced microglial LTB4 release is blocked by inhibiting elements of the sPLA2/AA/5-LOX/COX-2 pathway.

Effect of Aβ on microglial LTB4 release. As shown in FIG. 23, soluble Aβ$_{1-40}$ treatment of the murine microglial cell line, N9, results in an increased release of LTB4. Also shown in this figure is that COX-2 inhibition (via the COX-2 specific inhibitor, NS-398, 50 μM) results in complete blockade of LTB4 release. Furthermore, inhibition of p38 MAPK by the specific inhibitor SB202190 (5 μM) or inhibition of MEK1/2 via PD98059 (25 μM) each result in complete blockade of Aβ-induced microglial LTB4 release.

FIG. 23 shows that Aβ-induced microglial LTB4 release is blocked by inhibiting elements of the sPLA2/AA/5-LOX/COX-2 pathway. N9 microglial cells were treated as described in materials and methods. N=6 for control, n=5 for Aβ, n=5 for NS-398+Aβ, n=4 for SB202190+Aβ, and n=6 for PD98059+Aβ. ANOVA revealed significant treatment interactions between Aβ and drug x (p<0.001). One-way ANOVA revealed a significant difference between the Aβ treatment condition and control (p<0.001), but no significant differences were noted between drug x+Aβ and control (p>0.05), indicating complete blockade of Aβ-induced LTB4 release by inhibitors of elements of the PLA2/AA/5-LOX/COX-2 pathway.

Effect of Aβ on microglial [$^3$H]AA release.

Figure 24:
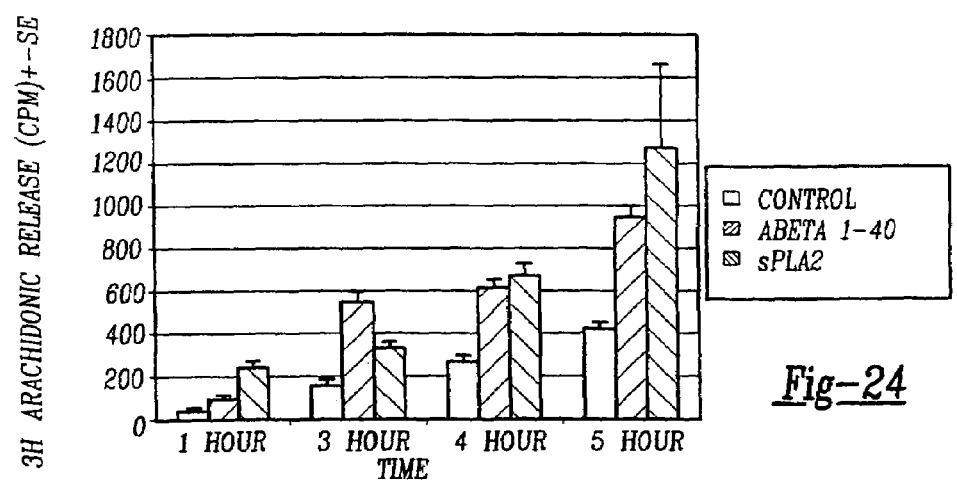
FIG. 24 is a graph showing that sPLA2 and Aβ induce [$^3$H]AA release in N9 microglia.

In order to determine if Aβ could stimulate PLA2 activity, resulting in increased release of AA, N9 microglia was incubated with [$^3$H]AA and then treated with sPLA2 or soluble Aβ$_{1-40}$. As shown in FIG. 24, secretory PLA2 induces the release of [$^3$H]AA, confirming the validity of such an assay to measure increased PLA2 activity. Most importantly, soluble Aβ$_{1-40}$ also stimulates AA release from N9 microglia, confirming that soluble Aβ activates the PLA2/AA/5-LOX/COX-2 pathway in microglia.

Additionally, FIG. 24 shows that sPLA2 and Aβ induce [$^3$H]AA release in N9 microglia. N9 microglia were treated as described in materials and methods. N=6 for each condition presented. ANOVA revealed significant main effects of Aβ treatment (p<0.001), sPLA2 treatment (p<0.001), and time (p<0.001). There were also significant interactive terms between time and either Aβ or sPLA2 treatment (p<0.001). T-test for independent samples showed significant differences in the means across time points between sPLA2 treatment and control (p<0.001), and between Aβ treatment and control (p<0.001).

Example 3

This example illustrates the effect of soluble Aβ on a neuronal model (NGF-β differentiated PC12 cells). The data presented here, like those in example 2, demonstrate that soluble Aβ peptides stimulate the sPLA2/AA/5-LOX/COX-2 pathway. In this example it is further highlighted that soluble Aβ peptides are able to trigger the pathway in various cell types.

Methods

Measurement of [$^3$H]AA release in neuronal cells (cultured differentiated PC12 cells). A rat pheochromocytoma cell line (PC12) was grown in Kahn's modification of F12 medium supplemented with 10% fetal calf serum, 100 U/mL penicillin and 0.1 µg/mL streptomycin. PC12 cells were seeded at 35,000 cells/well and differentiated with 60 ng/mL NGF-β for 5-6 days and then maintained with 5 ng/mL NGF-β thereafter. PC12 cells were treated with 0.4 µCi/mL of [$^3$H]AA for 18 h and were washed multiple times with 1 mL of complete medium to remove unincorporated [$^3$H]AA. Cells were then treated with 1 µM of Aβ$_{1-40}$ or 40 U/mL of sPLA2 for 5 h. Cell culture supernatants were collected each hour following treatment and radioactivity was quantified as described above.

Immunolocalization of activated p38 MAPK in neuronal cells. Cells were treated as described above, and were plated on glass cover-slips which had been soaked in 10 µg/mL of mouse laminin. Following differentiation, neuronal cells were treated with soluble Aβ$_{1-40}$ (5 µM) or anasomycin (20 µM, a known stimulator of p38 MAPK) for 10 and 20 min, and immediately fixed in 4% paraformaldehyde in 0.1 M PBS, pH 7.4 for 30 min at 4° C. Cells were washed multiple times in PBS, and incubated for 3 h with a phospho-specific antibody recognizing active active p38 MAPK. Cells were then washed multiple times in PBS and incubated with a secondary HRP-conjugated antibody. Immunostaining was performed using the DAKO ABC kit, cells were counter-stained with hematoxylin-eosin, and cells were then observed under a microscope.

Statistical analysis. Analysis of variance (ANOVA) was used to analyze the data, with post-hoc comparisons of means carried out where appropriate by Sheffe's or Bonferonni's methods. Levene's test for equality of variance followed by t-test for independent samples was used for single mean comparisons. Alpha levels were set at 0.05 for all analyses. Analyses were performed using SPSS for Windows release 9.5.

Results and Discussion

Figure 25:
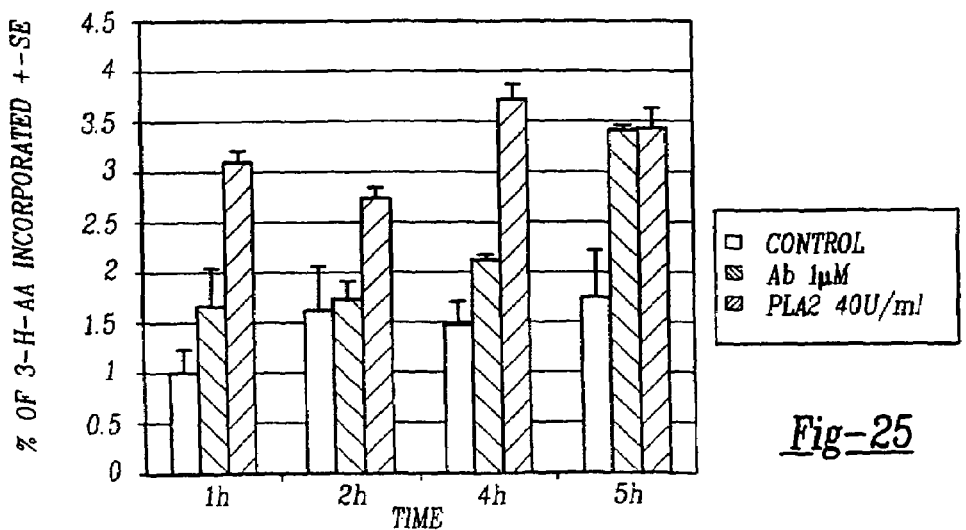
FIG. 25 is a graph showing that the soluble Aβ peptides induce [$^3$H]AA release in neuronal cells.
Figure 26A:
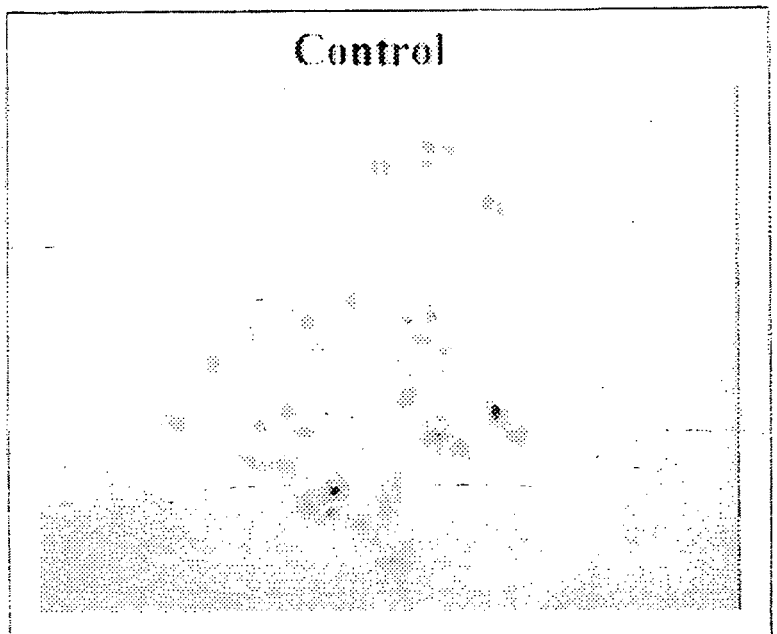
FIGS. 26(A-D) is a graph showing that the activation of p38 MAPK by soluble Aβ peptides in neuronal cells.
Figure 26B:
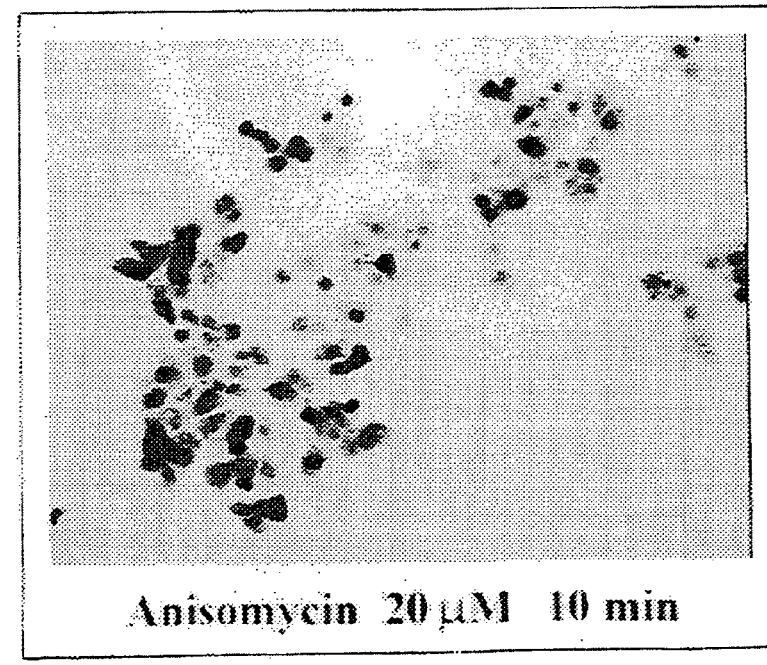
Figure 26C:
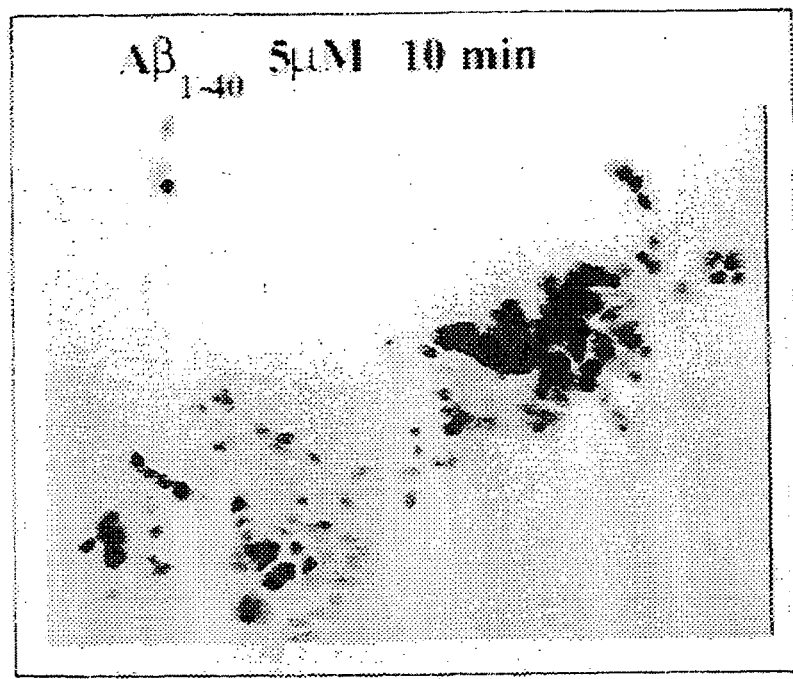
Figure 26D:
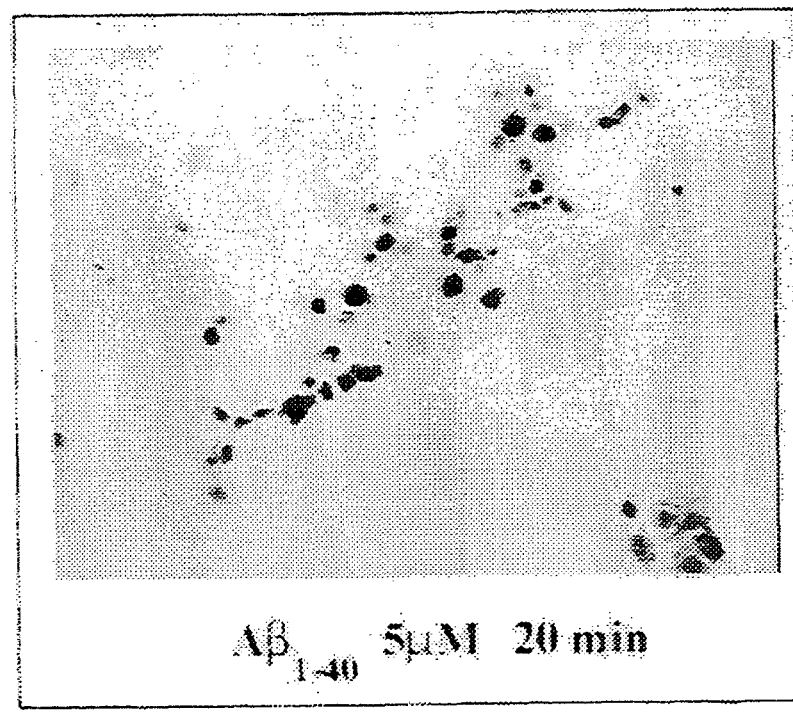

Soluble Aβ peptides induce [$^3$H]AA release in neuronal cells. Cultured differentiated PC12 cells were treated as described above, and, in order to determine if Aβ could stimulate PLA2 activity resulting in increased release of AA, cultured differentiated PC12 cells were incubated with [$^3$H]AA and then treated with sPLA2 or soluble Aβ$_{1-40}$. As shown in FIG. 25, secretory PLA2 induces the release of [$^3$H]AA, confirming the validity of such an assay to measure increased PLA2 activity. Most importantly, soluble Aβ$_{1-40}$ also stimulates AA release from neuronal cells, confirming that soluble Aβ activates the PLA2/AA/5-LOX/COX-2 pathway in these cells.

FIG. 25 shows the soluble Aβ peptides induce [$^3$H]AA release in neuronal cells. Cultured differentiated PC12 cells were treated as described in materials and methods. N=3 for each group presented. ANOVA revealed significant main effects of treatment with soluble Aβ peptides (p<0.001) and sPLA2 treatment (p<0.001). One-way ANOVA followed by post-hoc comparison revealed significant differences from 3 h onward between control and either sPLA2 treatment (p=0.001) or treatment with soluble Aβ peptides (p<0.01).

Soluble Aβ peptides activate p38 MAPK in neuronal cells. As shown in FIG. 26, soluble Aβ increases the phosphorylation of p38 MAPK, and induces the translocation from the cytosol to the nucleus in neuronal cells. Thus, soluble Aβ mimics the effect of anasomycin, a known stimulator of p38 MAPK, indicating that soluble Aβ activates p38 MAPK, an element of the PLA2/AA/5-LOX/COX-2 pathway.

Additionally, FIG. 26 shows the activation of p38 MAPK by soluble Aβ peptides in neuronal cells. Cultured differentiated PC12 cells were treated as described in materials and methods. Micrographs are at 40× magnification in brightfield. Brown staining reveals the intracellular location of activated p38 MAPK, and blue staining reveals the nucleus. In untreated (control) cells, little brown immunostaining is evident, and located essentially in the cytosol. In cells treated with either anisomycin or soluble Aβ peptides, brown immunostaining is intensified, and a strong nuclear staining is evident, showing that p38 MAPK is activated.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Abramovitz, M., E. Wong, M. E. Cox, C. D. Richardson, C. Li, and P. J. Vickers. 5-lipoxygenase-activating protein stimulates the utilization of arachidonic acid by 5-lipoxygenase. *Eur. J. Biochem.* 215:105-11, 1993.

Arita, H., K. Hanasaki, T. Nakano, S. Oka, H. Teraoka, and K. Matsumoto. Novel proliferative effect of phospholipase A2 in Swiss 3T3 cells via specific binding site. *J. Biol. Chem.* 266:19139-41, 1991.

Basso, D., C. Fabris, M. P. Panozzo, T. Meggiato, G. Del Favero, and R. Naccarato. Serum phospholipase A2 activity in chronic pancreatic diseases. *Clin. Biochem.* 23:229-32, 1990.

Borsch-Haubold, A. G., S. Pasquet, and S. P. Watson. Direct inhibition of cyclooxygenase-1 and -2 by the kinase inhibitors SB 203580 and PD 98059. SB 203580 also inhibits thromboxane synthase. *J. Biol. Chem.* 273:28766-72, 1998.

Clark, J. D., L. L. Lin, R. W. Kriz, C. S. Ramesha, L. A. Sultzman, A. Y. Lin, N. Milona, and J. L. Knopf. A novel arachidonic acid-selective cytosolic PLA2 contains a Ca(2+)-dependent translocation domain with homology to PKC and GAP. *Cell* 65:1043-1051, 1991.

Coria, F., A. Moreno, I. Rubio, M. A. Garcia, E. Morato, and F. Mayor. The cellular pathology associated with Alzheimer b-amyloid deposits in non-demented aged individuals. *Neuropathol. Appl. Neurobiol.* 19:261-268, 1993.

Crawford, F., Z. Suo, C. Fang, and M. Mullan. Characteristics of the in Vitro Vasoactivity of beta-amyloid peptides. *Exp. Neurol.* 150:159-168, 1998.

Dennis, E. A., S. G. Rhee, M-M. Billah, and Y. A. Hannun. Role of phospholipase in generating lipid second messengers in signal transduction. *FASEB J.* 5:2068-77, 1991.

Dennis, E. A. The growing phospholipase A2 superfamily of signal transduction enzymes. *Trends Biochem. Sci.* 22:1-2, 1997.

Duara, R., C. Grady, J. Haxby, M. Sundaram, N. R. Cutler, L. Heston, A. Moore, N. Schlageter, S. Larson, and S. I. Rapoport. Positron emission tomography in Alzheimer's disease. *Neurology* 36:879-887, 1986.

Dudley, D. T., L. Pang, S. J. Decker, A. J. Bridges, and A. R. Saltiel.. A synthetic inhibitor of the mitogen-activated protein kinase cascade. *Proc. Natl. Acad. Sci. USA* 92:7686-9, 1995.

Ellis, R. J., J. M. Olichney, L. J. Thal, S. S. Mirra, J. C. Morris, D. Beekly, and A. Heyman. Cerebral amyloid angiopathy in the brains of patients with Alzheimer's disease: the CERAD experience, Part XV. *Neurology* 46:1592-6, 1996.

Farooqui, A. A., S. I. Rapoport, and L. A. Horrocks. Membrane phospholipid alterations in Alzheimer's disease: deficiency of ethanolamine plasmalogens. *Neurochem. Res.* 22:523-7, 1997.

Frossard, P M, and Lestringant, G G (1995). Association between a dimorphic site on chromosome 12 and clincial diagnosis of hypertension in three independent populations. *Clin Genet* 48:284-287.

Futaki, N., S. Takahashi, M. Yokoyama, I. Arai, S. Higuchi, and S. Otomo. NS-398, a new anti-inflammatory agent, selectively inhibits prostaglandin G/H synthase/cyclooxygenase (COX-2) activity in vitro. *Prostaglandins* 47:55-9, 1994.

Glover, S., M. S. de Carvalho, T. Bayburt, M. Jonas, E. Chi, C. C. Leslie, and M. H. Gelb. Translocation of the 85-kDa phospholipase A2 from cytosol to the nuclear envelope in rat basophilic leukemia cells stimulated with calcium ionophore or IgE/antigen. *J. Biol. Chem.* 270:15359-67, 1995.

Gravitt, K. R., N. E. Ward, and C. A. O'Brian.. Inhibition of protein kinase C by melittin: antagonism of binding interactions between melittin and the catalytic domain by active-site binding of MgATP. *Biochem. Pharmacol.* 47:425-7, 1994.

Griffin, W. S. T., J. G. Sheng, G. W. Roberts, and R. E. Mrak. Interleukin-1 expression in different plaque types in Alzheimer's disease: significance in plaque evolution. *J. Neuropathol. Exp. Neurol.* 54:276-281, 1995.

Han, S. K., B. I. Lee, and W. Cho. Bacterial expression and characterization of human pancreatic phospholipase A2. *Biochim. Biophys. Acta.* 1346:185-92, 1997.

Hanasaki, K., Y. Yokota, J. Ishizaki, T. Itoh, and H. Arita. Resistance to endotoxic shock in phospholipase A2 receptor-deficient mice. *J. Biol. Chem.* 272:32792-7, 1997.

Hernandez, M., S. L. Burillo, M. S. Crespo, and M. L. Nieto. Secretory phospholipase A2 activates the cascade of mitogen-activated protein kinases and cytosolic phospholipase A2 in the human astrocytoma cell line 1321N1. *J. Biol. Chem.* 27-3:606-12, 1998.

Husain, S., and A. A. Abdel-Latif. Role of protein kinase C alpha in endothelin-1 stimulation of cytosolic phospholipase A2 and arachidonic acid release in cultured cat iris sphincter smooth muscle cells. *Biochim. Biophys. Acta.* 1392:127-44, 1998.

Huwiler, A., G. Staudt, R. M. Kramer, and J. Pfeilschifter. Cross-talk between secretory phospholipase A2 and cytosolic phospholipase A2 in rat renal mesangial cells. *Biochim. Biophys. Acta.* 1348:257-72, 1997.

Iadecola, C., F. Zhang, K. Niwa, C. Eckman, S. K. Turner, E. Fischer, S. Younkin, D. R. Borchelt, K. K. Hsiao, and G. A. Carlson. SOD1 rescues cerebral endothelial dysfunction in mice overexpressing amyloid precursor protein. *Nat. Neurosci.* 2:157-61, 1999.

Ishizaki, J., K. Hanasaki, K. Higashino, J. Kishino, N. Kikuchi, O. Ohara, and H. J. Arita. Molecular cloning of pancreatic group I phospholipase A2 receptor. *Biol. Chem.* 269:5897-904, 1994.

Itagaki, S., P. L. McGeer, H. Akiyama, S. Zhu, and D. Selkoe. Relationship of microglia and astrocytes to amyloid deposits of Alzheimer disease. *J. Neuroimmunol.* 24:173-182, 1989.

Iversen, L. L., R. J. Mortishire-Smith, S. J. Pollack, and M. S. Shearman. The toxicity in vitro of beta-amyloid protein. *Biochem. J.* 311:1-16, 1995.

Iwamoto, N., K. Kobayashi, and K. Kosaka. The formation of prostaglandins in the postmortem cerebral cortex of Alzheimer-type dementia patients. *J. Neurol.* 236:80-4, 1989.

Jeandel, C., M. B. Nicolas, F. Dubois, F. Nabet-Belleville, F. Penin, and G. Cuny. Lipid peroxidation and free radical scavengers in Alzheimer's disease. *Gerontology* 35:275-82, 1989.

Johnson, K. A., S. T. Mueller, T. M. Walshe, R. J. English, and B. L. Holman. Cerebral perfusion imaging in Alzheimer's disease. Use of a single photon emission computed tomography and iofetamine hydrochloride I 123. *Arch. Neurol.* 44:165-168, 1987.

Joyce-Brady, M., J. B. Rubins, M. P. Panchenko, J. Bernardo, M. P. Steele, L. Kolm, E .R. Simons, and B. F. Dickey. Mechanisms of mastoparan-stimulated surfactant secretion from isolated pulmonary alveolar type 2 cells. *J. Biol. Chem.* 266:6859-65, 1991.

Kan, H., Y. Ruan, and K. U. Malik. Involvement of mitogen-activated protein kinase and translocation of cytosolic phospholipase A2 to the nuclear envelope in acetylcholine-induced prostacyclin synthesis in rabbit coronary endothelial cells. *Mol. Pharmacol.* 50:1139-47, 1996.

Kanemasa, T., K. Hanasaki, and H. Arita.. Migration of vascular smooth muscle cells by phospholipase A2 via specific binding sites. *Biochim. Biophys. Acta.* 1125:210-4, 1992.

Kishino, J., O. Ohara, K. Nomura, R. M. Kramer, and H. Arita. Pancreatic-type phospholipase A2 induces group II phospholipase A2 expression and prostaglandin biosynthesis in rat mesangial cells. *J. Biol. Chem.* 269:5092-8, 1994.

Klinker, J. F., K. L. Laugwitz, A. Hageluken, and R. Seifert. Activation of GTP formation and high-affinity GTP hydrolysis by mastoparan in various cell membranes. G-protein activation via nucleoside diphosphate kinase, a possible general mechanism of mastoparan action. *Biochem. Pharmacol.* 51:217-23, 1996.

Kundu, G. C., and A. B. Mukherjee. Evidence that porcine pancreatic phospholipase A2 via its high affinity receptor stimulates extracellular matrix invasion by normal and cancer cells. *J. Biol. Chem.* 272:2346-53, 1997.

Kuo, Y., M. Emmerling, C. Vigo-Pelfrey, T. C. Kasunic, J. B. Kirkpatrick, G. H. Murdoch, M. J. Ball, and A. Roher. Water-soluble Abeta (N-40, N-42) Oligomers in Normal and Alzheimer Disease Brains. *J. Biol. Chem.* 271:4077-4081, 1996.

Kuo, Y., M. Emmerling, H. Lampert, S. R. Hempelman, T. A. Kokjohn, A. S. Woods, R. J. Cotter, and A. Roher. High Levels of Circulating Abeta42 are Sequestered by Plasma Proteins in Alzheimer's Disease. *Biochem. Biophys. Res. Comm.* 257:787-791, 1999.

Lambeau, G., P. Ancian, J. Barhanin, and M. J. Lazdunski. Cloning and expression of a membrane receptor for secretory phospholipases A2. *Biol. Chem.* 269:1575-8, 1994.

Lehtonen, J. Y., J. M. Holopainen, and P. K. Kinnunen. Activation of phospholipase A2 by amyloid beta-peptides in vitro. *Biochemistry* 35:9407-14, 1996.

Lin, L. L., M. Wartmann, A. Y. Lin, J. L. Knopf, A. Seth, and R. J. Davis. cPLA2 is phosphorylated and activated by MAP kinase. *Cell* 72:269-78, 1993.

Lindahl, M., and C. Tagesson. Selective inhibition of group II phospholipase A2 by quercetin. *Inflammation* 17:573-82, 1993.

Lue, L. F., L. Brachova, W. H. Civin, and J. Rogers. Inflammation, Abeta deposition, and neurofibrillary tangle formation as correlates of Alzheimer's disease neurodegeneration. *J. Neuropathol. Exp. Neurol.* 55:1083-1088, 1996.

McGeer, P. L., M. Schulzer, and E. G. McGeer. Arthritis and anti-inflammatory agents as possible protective factors for Alzheimer's disease: a review of-17 epidemiologic studies. *Neurology* 47:425-432, 1996.

McGeer, P. L., and E. G. McGeer. Inflammation of the brain in Alzheimer's disease: implications for therapy. *J. Leukoc. Biol.* 65:409-15, 1999.

Minami, T., H. Tojo, Y. Shinomura, T. Komatsubara, Y. Matsuzawa, and M. Okamoto. Elevation of phospholipase A2 protein in sera of patients with Crohn's disease and ulcerative colitis. *Am. J. Gastroenterol.* 88:1076-80, 1993.

Morita, I., M. Schindler, M. K. Regier, J. C. Otto, T. Hori, D. L. DeWitt, and W. L. Smith. Different intracellular locations for prostaglandin endoperoxide H synthase-1 and -2. *J. Biol. Chem.* 270:10902-8, 1995.

Murakami, M., S. Shimbara, T. Kambe, H. Kuwata, M. V. Winstead, J. A. Tischfield, and I. Kudo. The functions of five distinct mammalian phospholipase A2S in regulating arachidonic acid release. Type IIa and type V secretory phospholipase A2S are functionally redundant and act in concert with cytosolic phospholipase A2. *J. Biol. Chem.* 273:14411-23, 1998.

Naidu, A., D. Quon, and B. Cordell. beta-Amyloid peptide produced in vitro is degraded by proteinases released by cultured cells. *J. Biol. Chem.* 270:1369-74, 1995.

Nakajima, M., K. Hanasaki, M. Ueda, and H. Arita. Effect of pancreatic type phospholipase A2 on isolated porcine cerebral arteries via its specific binding sites. *FEBS Lett* 309:261-4, 1992.

Nitsch, R. M., J. K. Blusztajn, A. G. Pittas, B. E. Slack, J. H. Growdon, and R. J. Wurtman. Evidence for a membrane defect in Alzheimer disease brain. *Proc. Natl. Acad. Sci. USA* 89:1671-5, 1992.

Nomura, K., H. Fujita, and H. Arita. Gene expression of pancreatic-type phospholipase-A2 in rat ovaries: stimulatory action on progesterone release. *Endocrinology* 135:603-9, 1994.

Okamoto, T., S. Takeda, Y. Murayama, E. Ogata, and I. Nishimoto. Ligand-dependent G protein coupling function of amyloid transmembrane precursor. *J. Biol. Chem.* 270:4205-8, 1995.

Paris, D., T. A. Parker, T. Town, Z. Suo, C. Fang, J. Humphrey, F. Crawford, and M. Mullan. Role of Peroxynitrite in the Vasoactive and Cytotoxic Effects of Alzheimer's beta-amyloid1-40 Peptide. *Exp. Neurol.* 152:116-122, 1998.

Paris, D., T. Town, T. A. Parker, J. Humphrey, and M. Mullan. Isoform-specific vasoconstriction induced by Apolipoprotein E and modulation of this effect by Alzheimer's beta-amyloid peptide. *Neurosci. Lett.* 256:73-76, 1998.

Paris, D., T. Town, T. A. Parker, J. Tan, J. Humphrey, F. Crawford, and M. Mullan. Inhibition of Alzheimer's beta-Amyloid Induced Vasoactivity and Proinflammatory Response in Microglia by a cGMP-Dependent Mechanism. *Exp. Neurol.* 157:211-221, 1999.

Rogers, J., L. C. Kirby, S. R. Hempielman, et al. Clinical trial of indomethacin in Alzheimer's disease. *Neurology* 43:1609-1611, 1993.

Selkoe, D. J. Amyloid beta-protein and the genetics of Alzheimer's disease. *J. Biol. Chem.* 271:18295-8, 1996.

Serhan, C. N., J. Z. Haeggstrom, and C. C. Leslie. Lipid mediator networks in cell signaling: update and impact of cytokines. *FASEB J.* 10:1147-58, 1996.

Siffert, W, Rosskopf, D, Siffert, G, Busch, S, Moritz, A, Erbel, R, Sharma, A M, Ritz, E, Wichmann, H E, Jakobs, K H, Horsthemke, B. Association of a human G-protein beta3 subunit variant with hypertension. *Nat Genet* 18:45-48.

Sisodia S. S., and D. L. Price. Role of the beta-amyloid protein in Alzheimer's disease. *FASEB J.* 9:366-70, 1995.

Stephenson, D. T., C. A. Lemere, D. J. Selkoe, and J. A. Clemens. Cytosolic phospholipase A2 (cPLA2) immunoreactivity is elevated in Alzheimer's disease brain. *Neurobiol. Dis.* 3:51-63, 1996.

Stewart, W. F., C. Kawas, M. Corrada, and E. J. Metter. Risk of Alzheimer's disease and duration of NSAID use. *Neurology* 48:626-632, 1997.

Suo, Z., J. Humphrey, A. Kundtz, F. Sethi, A. Placzek, F. Crawford, and M. Mullan. Soluble Alzheimer's beta-amyloid constricts the cerebral vasculature in vivo, *Neurosci. Lett.* 257:77-80, 1998.

Thomas, T., G. Thomas, C. McLendon, T. Sutton, and M. Mullan. beta-Amyloid-mediated vasoactivity and vascular endothelial damage. *Nature* 380:168-71, 1996.

Tischfield, J. A. A reassessment of the low molecular weight phospholipase A2 gene family in mammals. *J. Biol. Chem.* 272:17247-50, 1997.

Tohkin, M., J. Kishino, J. Ishizaki, and H. Arita. Pancreatic-type phospholipase A2 stimulates prostaglandin synthesis in mouse osteoblastic cells (MC3T3-E1) via a specific binding site. *J. Biol. Chem.* 268:2865-71, 1993.

Tsunoda, Y., and C. Owyang. The regulatory site of functional GTP binding protein coupled to the high affinity cholecystokinin receptor and phospholipase A2 pathway is on the G beta subunit of Gq protein in pancreatic acini. *Biochem. Biophys. Res. Commun.* 211:648-55, 1995.

Walker, D. G., O. Yasuhara, P. A. Patston, E. G. McGeer, and P. L. McGeer. Complement C1 inhibitor is produced by brain tissue and is cleaved in Alzheimer disease. *Brain. Res.* 675:75-82, 1995.

Wisniewski, H. M., and J. Weigel. Migration of perivascular cells into the neuropil and their involvement in beta-amyloid plaque formation. *Acta. Neuropathol. (Berl.)* 85:586-95, 1993.

Wisniewski, H. M., J. Wegiel, K. C. Wang, and B. Lach. Ultrastructural studies of the cells forming amyloid in the cortical vessel wall in Alzheimer's disease. *Acta. Neuropathol. (Berl.)* 84:117-27, 1992.

Zhu, M., C. H. Gelband, J. M. Moore, P. Posner, and C. Sumners. Angiotensin Type-2 Receptor Stimulation of Neuronal Delayed-Rectifier Potassium Current Involves Phospholipase A2 and Arachidonic Acid. *J. Neurosci.* 18:679-686, 1998.

What is claimed is:

1. A method of modifying beta-amyloid-induced vasoactivity in individuals with Alzheimer's Disease or other vascular-related diseases or disorders, in which said vascular-related diseases or disorders are selected from the group consisting of cerebral amyloid angiopathy, vascular amyloidosis, hypertension and vasospasm associated with severe post-traumatic head injury, comprising antagonizing the secretory phospholipase A2/arachidonic acid/5-lipoxygenase/cyclo-oxygenase-2 pro-inflammatory pathway by administering a pharmaceutically effective amount of oleyloxyethylphosphocholine to the individual in an amount ranging from between 0.1 µg to 10 mg/kg body weight/day.

2. The method according to claim 1, further defined as down-regulating a soluble Aβ pro-inflammatory pathway.

3. The method of claim 1, wherein the vascular-related disease or disorder is cerebral amyloid angiopathy.

4. The method of claim 1, wherein the vascular-related disease or disorder is vascular amyloidosis.

5. The method of claim 1, wherein the vascular-related disease or disorder is hypertension.

6. The method of claim 1, wherein the vascular-related disease or disorder is vasospasm associated with severe post-traumatic head injury.

7. The method of claim 1, wherein oleyloxyethylphosphocholine is administered orally, subcutaneously, parenterally, intraperitoneally, intranasally or by implant.

8. The method of claim 1, wherein oleyloxyethylphosphocholine is administered orally.

9. The method of claim 8, wherein oleyloxyethylphosphocholine is administered in a pharmacological formulation in the form of a tablet, suspension, solution, emulsion, capsule, powder, or syrup.

10. A method of treating cerebral amyloid angiopathy, vascular amyloidosis, hypertension or vasospasm associated with severe post-traumatic head injury in an individual, the method comprising administering a pharmaceutically effective amount of oleyloxyethylphosphocholine to the individual.

* * * * *